(12) United States Patent
Piskun

(10) Patent No.: US 11,944,311 B2
(45) Date of Patent: *Apr. 2, 2024

(54) RUBBER BAND LIGATION SYSTEM FOR TREATMENT OF HEMORRHOIDS

(71) Applicant: Gregory Piskun, Delray Beach, FL (US)

(72) Inventor: Gregory Piskun, Delray Beach, FL (US)

(*) Notice: Subject to any disclaimer, the term of this patent is extended or adjusted under 35 U.S.C. 154(b) by 170 days.

This patent is subject to a terminal disclaimer.

(21) Appl. No.: 17/168,803

(22) Filed: Feb. 5, 2021

(65) Prior Publication Data
US 2021/0177424 A1 Jun. 17, 2021

Related U.S. Application Data

(63) Continuation of application No. 16/125,561, filed on Sep. 7, 2018, now Pat. No. 10,925,609.
(Continued)

(51) Int. Cl.
*A61B 17/12* (2006.01)
*A61B 1/018* (2006.01)
(Continued)

(52) U.S. Cl.
CPC ........ *A61B 17/12013* (2013.01); *A61B 1/018* (2013.01); *A61B 1/31* (2013.01); *A61B 1/32* (2013.01); *A61B 17/30* (2013.01); *A61B 17/3423* (2013.01); *A61B 2017/00477* (2013.01); *A61B 2017/00544* (2013.01); *A61B 2017/00818* (2013.01); *A61B 2017/12018* (2013.01); *A61B 2017/306* (2013.01);
(Continued)

(58) Field of Classification Search
CPC ..... A61B 17/12013; A61B 1/018; A61B 1/31; A61B 1/32; A61B 17/30; A61B 17/3423; A61B 2017/00477; A61B 2017/00544; A61B 2017/00818; A61B 2017/12018; A61B 2017/306; A61B 2017/3452; A61B 2090/034; A61B 2090/061; A61B 2090/0807; A61B 2090/0811
USPC .................................................. 600/37, 101
See application file for complete search history.

(56) References Cited

U.S. PATENT DOCUMENTS 4,819,620 A 4/1989 Okutsu
4,834,067 A 5/1989 Block
(Continued)

FOREIGN PATENT DOCUMENTS

| CN | 202 198 567 | 4/2012 |
|---|---|---|
| JP | 62 82934 | 4/1987 |
| WO | WO 2007/116327 | 10/2007 |

OTHER PUBLICATIONS

International Search Report and Written Opinion dated Jan. 8, 2019 for International Application No. PCT/US2018/050096.
(Continued)

*Primary Examiner* — Sunita Reddy
(74) *Attorney, Agent, or Firm* — Neil D. Gershon

(57) ABSTRACT

A system including an anoscope having a first channel extending along a longitudinal axis and a second channel positioned at an angle to the first channel. For hemorrhoid treatment, an elastic band ligation device is insertable into the second channel, the elastic band ligation device carrying an elastic band and having an advancer movable in a distal direction to dislodge the elastic band.

19 Claims, 20 Drawing Sheets

Related U.S. Application Data

(60) Provisional application No. 62/566,255, filed on Sep. 29, 2017.

(51) Int. Cl.
  *A61B 1/31* (2006.01)
  *A61B 1/32* (2006.01)
  *A61B 17/00* (2006.01)
  *A61B 17/30* (2006.01)
  *A61B 17/34* (2006.01)
  *A61B 90/00* (2016.01)

(52) U.S. Cl.
  CPC . *A61B 2017/3452* (2013.01); *A61B 2090/034* (2016.02); *A61B 2090/061* (2016.02); *A61B 2090/0807* (2016.02); *A61B 2090/0811* (2016.02)

(56) References Cited

U.S. PATENT DOCUMENTS

| | | | |
|---|---|---|---|
| 5,158,563 | A | 10/1992 | Cosman |
| 5,741,273 | A | 4/1998 | O'Regan |
| 7,029,438 | B2 | 4/2006 | Morin et al. |
| 7,118,528 | B1 | 10/2006 | Piskun |
| 2002/0111639 | A1* | 8/2002 | Armstrong ............... A61B 1/31 606/144 |
| 2003/0130559 | A1 | 7/2003 | Piskun |
| 2003/0163026 | A1 | 8/2003 | Fontana |
| 2003/0187464 | A1 | 10/2003 | Tolkoff |
| 2006/0009797 | A1 | 1/2006 | Armstrong |
| 2006/0020241 | A1 | 1/2006 | Piskun |
| 2006/0036129 | A1 | 2/2006 | Sias |
| 2006/0259041 | A1 | 11/2006 | Hoffman |
| 2006/0264706 | A1 | 11/2006 | Piskun |
| 2008/0255519 | A1* | 10/2008 | Piskun ............... A61B 17/3439 600/109 |
| 2008/0262511 | A1* | 10/2008 | Delaney ................... A61B 1/31 600/184 |
| 2008/0275306 | A1 | 11/2008 | Rebuffat |
| 2009/0005647 | A1 | 1/2009 | Bozdag |
| 2009/0318940 | A1 | 12/2009 | Piskun |
| 2010/0010296 | A1 | 1/2010 | Piskun |
| 2010/0063517 | A1 | 3/2010 | Cleator |
| 2010/0145148 | A1 | 6/2010 | Wenchell |
| 2011/0087075 | A1 | 4/2011 | Wenchell |
| 2011/0224494 | A1 | 9/2011 | Piskun |
| 2012/0150196 | A1 | 6/2012 | Hoffman |
| 2013/0110139 | A1 | 5/2013 | Piskun |
| 2014/0121679 | A1 | 5/2014 | Cleator |
| 2014/0200404 | A1 | 7/2014 | Piskun |
| 2014/0249550 | A1 | 9/2014 | Mullins |
| 2015/0045616 | A1 | 2/2015 | Piskun |
| 2015/0057678 | A1 | 2/2015 | Chotenovsky et al. |
| 2015/0057679 | A1 | 2/2015 | Chotenovsky et al. |
| 2015/0057680 | A1 | 2/2015 | Chotenovsky et al. |
| 2015/0272564 | A1 | 10/2015 | Piskun |
| 2016/0038015 | A1 | 2/2016 | Wenchell |
| 2016/0038016 | A1* | 2/2016 | Wenchell ............ A61B 17/0469 600/184 |
| 2016/0106435 | A1 | 4/2016 | Brenner |
| 2016/0157866 | A1 | 6/2016 | Chotenovsky et al. |

OTHER PUBLICATIONS

European Search Report dated Jan. 19, 2021, for International Application No. 18782244.0.

* cited by examiner

RUBBER BAND LIGATION SYSTEM FOR TREATMENT OF HEMORRHOIDS

This application is a continuation of application Ser. No. 16/125,561, filed Sep. 7, 2018, which claims priority from provisional application Ser. No. 62/566,255, filed Sep. 29, 2017, the entire contents of which are incorporated herein by reference.

BACKGROUND OF THE INVENTION

1. Field of the Invention

This application relates to a system and method for treatment of hemorrhoids.

2. Background

Internal hemorrhoids are normal, asymptomatic rectal vascular tissue. There are typically three or more internal hemorrhoids, which play a role in reducing the anal trauma during defecation and aiding in gas and stool continence. When hemorrhoids, however, enlarge and/or their surface becomes fragile (due to inflammation, infection, or other factors), they may bleed and/or prolapse outside of the anus, which may cause discomfort, pain, anemia, and other disturbing symptoms.

One of the common treatment methods of symptomatic hemorrhoids is referred to as "rubber band ligation" which involves strangulation of the hemorrhoid itself and/or strangulation of its superior blood supply by a special elastic rubber ring (band). The rubber band is placed onto the target tissue using a rubber band ligator in the painless area of the anal canal, which is located anatomically proximal of ("above") the so-called dentate line. The dentate line is a visible anatomical line separating the sensitive mucosa (located distally to the dentate line) from the non-sensitive (or less sensitive) mucosa (located proximally to the dentate line). In the following few days after the rubber band placement, the tissue strangulated by the rubber band becomes necrotic and falls off leaving a corresponding tissue defect, which then heals over the following weeks. If performed properly, this technique leads to the decreased blood supply to the internal hemorrhoid and/or reduction of its size, resulting in improvement of the associated hemorrhoidal symptoms.

Although, overall, the rubber band ligation technique for the treatment of symptomatic internal hemorrhoids is considered fairly straightforward among experts, there are a number of technical and anatomical challenges and nuances which challenge an acquisition of the technical mastery. First, proper placement of the rubber band is critical. If the rubber band is placed too close to the dentate line (either distally or proximally) or too close to the underlying rectal muscle, it may lead to undesirable side effects such as severe pain, tenesmus, and or fainting, and can even in some instances lead to severe complications such as rectal perforation, infection, and/or severe bleeding. To avoid or minimize complications of the rubber band ligation procedure, the rubber band should be placed 2-2.5 cm proximally to the visualized dentate line in the non-sensitive area without any involvement of the underlying rectal muscle.

In addition, the rubber band ligation technique requires an assistant which thereby requires coordination. That is, the technique requires an accurate and well-controlled release of the rubber band by the operator in the restricted field with limited view while orchestrating this important maneuver with the assistant's movements.

One of the main technical challenges for an operator during the rubber band ligation technique is related to the need, while holding an anoscope, to pull on the target tissue with either forceps or the suction tip and then, when "just the right amount" of the target tissue appears to be engaged, to release the rubber band onto the base of the pulled tissue. These maneuvers require coordinated manipulations of both hands of the operator and possibly an assistant holding the anoscope. In addition, the view of the target area can be obscured by the instruments and the operator's own hands, further increasing the challenge of the procedure.

While special hemorrhoidal forceps can provide the most accurate tissue manipulation for application of elastic bands, the forceps require a fairly advanced, expert dexterity. As an alternative, tissue suction can be utilized, however, it requires dedicated suction equipment, which in turn requires access to an electrical source, the need for single use components, and costly professional support and maintenance. Further, the amount of the suctioned tissue may need to vary from case to case, and the suction provided by the typical suction equipment is not sufficiently gauged to address this variable need. There is also no ability in the typical suction equipment to "slightly release" the suctioned tissue. This frequently leads to the excessive tissue suction or repetitive repositioning of the suction tip until "just the right amount" of the target tissue is engaged for rubber banding. Thus, in prior techniques, the operator cannot fully control the amount of tissue suctioned.

In current procedures, an anoscope is inserted through the anal canal and instruments for treating the hemorrhoids are inserted through a channel of the anoscope to access the target hemorrhoidal tissue. However, a current problem includes a lack of technology for organizing and stabilizing the instruments within the anoscope. Also, in current instrumentation, the instruments often obstruct the clinician's view as the clinician tries to view the tissue through the anoscope channel. Not only can current instruments block the surgeon's direct view but their stabilization relies on the clinician holding the instrument position during manipulation of the instrument. Holding the instrument in position becomes more challenging as components of the instrument are moved in an axial direction. If the axial position is not maintained and the instrument moves during the procedure, its distance from the dentate line will change which results in the risks enumerated above. Thus, a clinician would like to have a view of the working space that is the least obstructed as well as a system that can better ensure the desired position of the instrument is maintained during the procedure.

Therefore, there is a need for improvements to the rubber band ligation device and method, which would facilitate the accurate rubber band placement by an operator without requiring advanced manual skills. In addition, it would be further beneficial to eliminate the need for an assistant during the procedure which would not only reduce the cost of the procedure but avoid the risk of non-coordination of the operator and assistant. Moreover, there is a need to improve tissue manipulation as well as a need to improve stabilization of the instruments and visibility of the target area during the procedure.

SUMMARY OF THE INVENTION

The present invention overcomes the deficiencies and disadvantages of the prior art. The present invention advantageously provides a system for treating hemorrhoid tissue which provides a stabilizing platform for treatment devices such as ligating instruments. The systems disclosed herein achieve such stabilization with minimizing obstruction of visibility. The systems disclosed herein also simplify the procedure. Advantages of the systems can be appreciated by the detailed description herein.

In one aspect, the present invention provides a system for treatment of hemorrhoids comprising an anoscope having a first channel extending along a longitudinal axis and a second channel positioned at an angle to the first channel. An elastic band ligation device is insertable into the second channel and carries an elastic band and has an advancer movable in a distal direction to dislodge the elastic band.

In some embodiments, an obturator is removably insertable into the first channel to aid insertion of the anoscope into the rectum.

In some embodiments, the elastic band ligation device comprises a plunger movable in a proximal direction within a tube of the device to effect suctioning of target tissue. The elastic band in some embodiments is positioned on an external surface of the device and the elastic band ligation device can include a tube and the advancer can be positioned external and concentric with the tube.

The system can include a first stop on a wall of the anoscope to restrict distal movement of the ligation device within the second channel and/or a second stop on the anoscope to restrict proximal movement of the ligation device in the second channel. In some embodiments, rotation of the ligation device relative to the anoscope in a first direction enables the second stop to limit proximal movement. In some embodiments, rotation of the ligation device relative to the anoscope in a first direction enables engagement with a portion of the internal wall to limit proximal movement of the ligating device.

The anoscope can have a marker to indicate a distance from a dentate line of a patient.

In some embodiments, the second channel has a longitudinally extending opening facing inferiorly; in other embodiments the second channel has a longitudinally extending channel facing laterally. In some embodiments, the second channel has fenestrations which can provide discrete spaced apart channel sections.

In accordance with another aspect of the present invention, a system for treatment of hemorrhoids is provided comprising an anoscope having a first channel extending along a longitudinal axis and a second channel positioned at an angle to the first channel, the second channel intersecting the first channel so a distal opening of the second channel is in communication with the first channel. An elastic band ligation device is insertable into the second channel, the elastic band ligation device including a first tube and a tissue holder. The first tube is movable to advance and dislodge an elastic band from the ligation device onto target tissue. The second channel stabilizes the ligation device and restricts lateral movement while enabling longitudinal movement within the second channel and the second channel enables access to the target tissue at an angle to a longitudinal axis of the first channel. In some embodiments, the first tube is an outer tube movable with respect to a second tube inside the first tube.

In some embodiments, the tissue holder comprises a suction device. The suction device can include a plunger having a transverse distal plate wherein proximal movement of the plunger pulls the target tissue proximally as the outer tube engages the target tissue. In some embodiments, a locking device is provided which includes an engagement structure on the ligation device engagable with engagement structure of the anoscope to restrict axial movement of the ligation device within the anoscope. In some embodiments, engagement structure on the ligation device and anoscope restrict rotational movement of the ligating device within the anoscope.

In accordance with another aspect of the present invention, a system for stabilizing an instrument during a hemorrhoid treatment procedure is provided comprising an anoscope having a first channel extending along a longitudinal axis to provide direct visualization to a clinician through a length of the first channel and a second channel positioned at an angle to a longitudinal axis of the first channel to direct instrumentation inserted through the second channel at an angle to a distal end of the first channel to reduce obstruction of direct visualization through the first channel. The second channel further has an engagement structure engageable with an instrument inserted therethrough to restrict axial movement of the instrument to thereby maintain the axial position of the instrument with respect to a dentate line of a patient.

In some embodiments, the second channel includes structure to limit rotation of an instrument within the second channel. In some embodiments, a wall of the second channel is non-continuous to provide openings for visualization of the instrument during insertion through the second channel.

In accordance with another aspect of the present invention, an anoscope is provided having an outer wall dimensioned and configured for insertion into the anal canal, the anoscope having a proximal end, a distal end, a first channel and a second channel. The first channel extends longitudinally through the anoscope and has a proximal opening and a distal opening. The second channel is positioned at an angle to a longitudinal axis of the first channel and has a proximal opening and a distal opening, the distal opening of the second channel communicating with the first channel and the second channel dimensioned and configured to receive a treatment device such as a ligation device.

In some embodiments, the anoscope includes a stop to limit distal movement and/or limit proximal movement of a ligation device inserted through the second channel. The anoscope can also in some embodiments limit rotational movement of a ligation device positioned in the second channel.

In some embodiments, the second channel is on a first side of the anoscope and a distal end of the anoscope forms a window on a second side, wherein a distal edge on the first side is distal of an opposing edge of the anoscope on the second side. In some embodiments, the first and second channels share a common wall. In some embodiments, the second channel has a wall having a plurality of fenestrations to provide a series of spaced discrete longitudinally aligned channels. In some embodiments, the second channel includes a longitudinally extending slot to enable lateral insertion of the ligation device into the second channel.

In accordance with another aspect of the present invention, an elastic band ligation device is provided comprising a first tube, a plunger positioned within the first tube, and a second tube positioned over the first tube. The first tube is configured to hold an elastic band in tension, wherein the plunger is retractable to suction hemorrhoid tissue and pull hemorrhoid tissue proximally, and the second tube is advanceable to advance the elastic band from the first tube onto the target tissue, The device in some embodiments includes an engagement member for interacting with an engagement surface on an anoscope through which the device is insertable to restrict movement of the device within the anoscope. The device can include a marker for indicating a distance from a dentate line of a patient.

In some embodiments, the second tube has a distal edge which contacts the tensioned elastic band to advance it from the first tube. The plunger in some embodiments has a transverse plate at a distal end to engage the hemorrhoid tissue.

In accordance with another aspect of the present invention, a method for applying an elastic band to hemorrhoidal tissue is provided comprising:
a) providing an anoscope having a first longitudinal channel and a second channel extending at an angle to the first channel;
b) inserting the anoscope through the anal canal adjacent hemorrhoid tissue and anatomically proximal of a dentate line of a patient;
c) inserting a ligating device through the second channel of the anoscope; and
d) advancing the elastic band from the ligating device onto the hemorrhoid tissue.

In some embodiments, the step of advancing the elastic band comprises the step of advancing an outer tube of the ligating device in contact with the elastic band.

In some embodiments, the method includes step of locking the ligating device to the anoscope to restrict axial and/or rotational movement of the ligating device within the anoscope. In some embodiments, the ligating device is rotatable with respect to the anoscope to engage the locking device to restrict axial movement.

In some embodiments, the method further comprises the step of retracting an inner member of the ligating device to suction the hemorrhoid tissue and retract the hemorrhoid tissue into the ligating device. The step of advancing the elastic band is preferably performed subsequent to the step of retracting the inner member to suction the hemorrhoid tissue.

In some embodiments, the step of inserting the ligating device includes advancing the device through the second channel until it contacts a stop of the anoscope.

In some embodiments, the method includes the step of visualizing the ligating device though an opening in the second channel as it is advanced through the second channel. In some embodiments, the step of inserting the ligating device through the second channel includes inserting the ligating device through a proximal opening in the second channel; in other embodiments, the step of inserting the ligating device through the second channel includes inserting the ligating device laterally through a longitudinally extending opening in the second channel.

In some embodiments, the anoscope and second channel are configured so that when the anoscope is inserted so a distal edge is at the dentate line, a tip of the ligating device inserted through the second channel to contact the target tissue will be positioned about 2 cm to about 2.5 cm from the distal edge of the anoscope and the dentate line of the patient. In some embodiments, a vertex of an imaginary triangle formed by an intersection of an extended longitudinal axis of the second channel and an extended edge of the anoscope is between about 2 cm and about 2.5 cm from the dentate line of the patient.

BRIEF DESCRIPTION OF THE DRAWINGS

So that those having ordinary skill in the art to which the subject invention appertains will more readily understand how to make and use the surgical apparatus disclosed herein, preferred embodiments thereof will be described in detail hereinbelow with reference to the drawings, wherein.

DETAILED DESCRIPTION OF PREFERRED EMBODIMENTS

Figure 1:
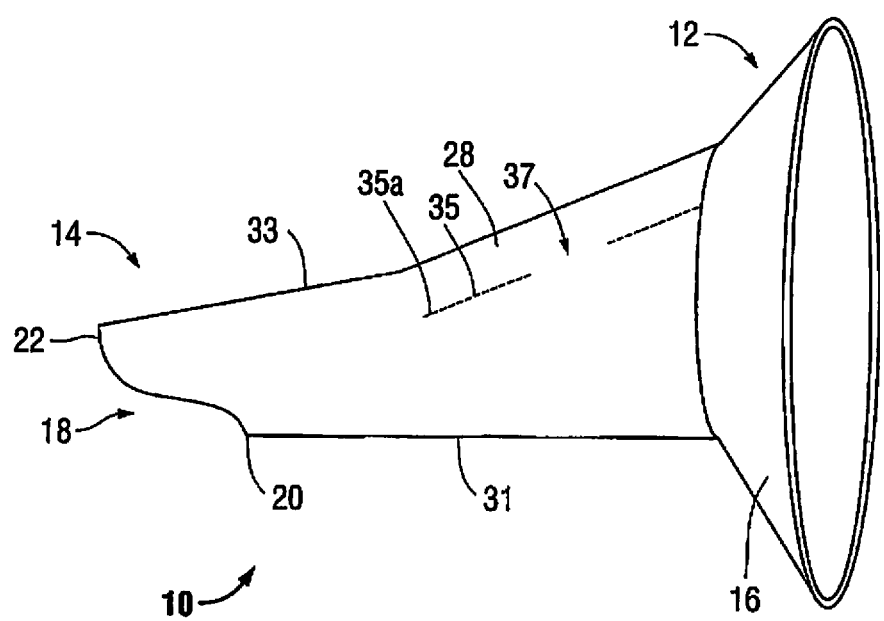
FIG. 1 is a side perspective view of a first embodiment of the anoscope of the present invention.

The systems and methods of the present invention simplify the rubber band ligation procedure and advantageously eliminate the need for an assistant. The systems of the present invention also improve the organization and stability of the instrumentation to enable wider physician use of the system. Further, the systems of the present invention improve the clinician's visibility of the target tissue. The systems disclosed herein achieve the foregoing by providing a) an anoscope with a dedicated channel for a ligating device or other instruments (devices); and b) a ligating device (instrument) insertable though the dedicated channel. The ligating device (also referred to herein as the ligation device or ligator) can in some embodiments in and of itself suction the target hemorrhoidal tissue and apply an elastic band to the hemorrhoidal tissue. The ligating device can also in some embodiments lock to the anoscope, thereby freeing a hand of the operator or assistant which would otherwise have to hold the components and also ensuring the critical positioning of the ligating device relative to the dentate line is maintained during the procedure. The tissue suctioning and holding capabilities of the ligating device of these embodiments also improve tissue manipulation. The features of the anoscope and ligating device of the present invention are discussed in detail below, along with the method of use.

Thus, the technology taught herein provides one or more of 1) an organization of the hemorrhoid treatment instrument (s), such as a ligating device, e.g., a rubber band ligator, to maximize stability and maneuverability and visualization of the hemorrhoidal tissue; 2) interlocking components to restrict movement of the hemorrhoid treatment instrument to free a hand of the clinician and to maintain positioning of the instrument, especially with respect to the sensitive dentate line; 3) simplification of the system to better ensure consistent clinical results so the procedure is not dependent on the skills of the clinician and that the system is available to a wider range of clinicians to utilize; and 4) minimization of instrumentation utilized for treatment of hemorrhoids. It should be appreciated that having such improvements reduces the technical complexity and increases the efficacy and safety of otherwise more complex hemorrhoid tissue treatment procedures.

It should be appreciated that the present invention provides an anoscope, a ligating device and/or a system comprising an anoscope and a ligating device. However, it is also contemplated that a different ligating device or other instrumentation can be used with the anoscope of the present invention, i.e., inserted through the dedicated channel of the anoscope. It is also contemplated that the ligating device (ligator) of the present invention can be used with anoscopes other than those of the present invention disclosed herein. Thus, various embodiments of the anoscopes of the present invention will be discussed initially, followed by a discussion of the ligation instrument of the present invention and then followed by a description of the method of use.

Turning first to the anoscope, several embodiments of the anoscope are disclosed herein. The commonality of the anoscopes is the feature of a channel angled with respect to the longitudinal axis of the main channel of the anoscope. The channels can be of various lengths, of various configurations and can have slots at various locations. These different embodiments are discussed in detail below.

With regard to the anoscopes and ligating devices disclosed herein, the proximal portion is considered the portion or region closer to the user and the distal portion is considered the portion or region further from the user. However, when referring to the anatomy, e.g., the anal canal and the hemorrhoidal tissue, the proximal portion is the portion or region closer to the head or heart of the patient and the distal portion is the portion or region further from the head or heart of the patient. Thus, when discussing the anatomy, the distal end of the ligating device is placed proximal (further inwardly or "above") the dentate line of the patient. To help with understanding, as used herein when referring to the anatomy, "anatomically distally/anatomically proximally" will be used to differentiate from distal/proximal of the instruments and anoscopes.

Figure 3A:
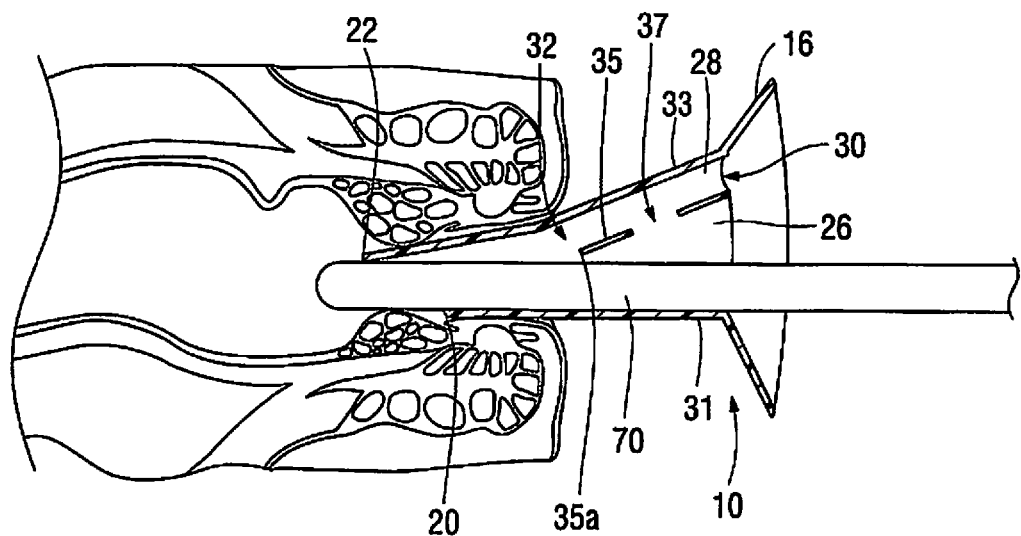
FIG. 3A is a cross-sectional view showing an obturator positioned within the main channel of the anoscope of FIG. 1 to aid insertion through the anal canal to access the target hemorrhoidal tissue.

Referring now in detail to the drawings wherein like reference numerals identify similar or like components, FIG. 1 illustrates one embodiment of the anoscope (also referred to as a cannula) of the present invention, shown in cross-section in FIG. 3A. The anoscope is designated generally by reference numeral 10 and includes a proximal portion 12 and a distal portion 14, the wall of the anoscope tapering toward the distal portion 14.

A proximal flange 16 of anoscope 10 provides a wider rim that prevents insertion of anoscope 10 fully into the anal canal and facilitates gripping by the clinician. The anoscope 10 includes a window 18 at the distal portion 14, the window 18 providing access to the target hemorrhoid tissue for the ligating device extending through the anoscope as described below. As shown, the distal end of anoscope 10 has a distal edge 20 and a distal edge 22 on opposing sides of a longitudinal axis of the anoscope, the distal edge 20 spaced axially proximally of the distal edge 22. Stated another way, the distal portion 14 of the anoscope 10 is angled so that a distal edge 20 of the wall 31 adjacent the window 18 is proximal of the distal edge 22 of the wall 33 opposite the window 18. The distal end has a curved contour as shown.

The anoscope 10 has a channel (also referred to herein as a lumen) 26 dimensioned and configured to receive an obturator such as obturator 70 of FIG. 3A. The channel 26 extends along a longitudinal axis of the anoscope 10 and can be considered the main channel (lumen) of the anoscope. In the illustrated embodiment, channel 26 has a transverse cross-section varying in diameter and shape along its length, however, different shaped channels and different shaped cross-sections, e.g., circular, oval, asymmetric, etc. are contemplated and can be uniform or change (non-uniform) along the length. Anoscope 10 also includes an angled channel (also referred to herein as a lumen) 28. Channel 28 forms an internal channel for receiving an instrument (device), i.e., for insertion of the ligating device described below or other hemorrhoid treatment devices, and is therefore also referred to herein as instrument channel. In the illustrated embodiment, channel 28 is cylindrical with a circular transverse cross-section, however, different shaped channels and different shaped cross-sections, e.g., oval, are also contemplated. Instrument channel 28 is preferably smaller in diameter than main channel 26. It is also preferably shorter in length.

Figure 4:
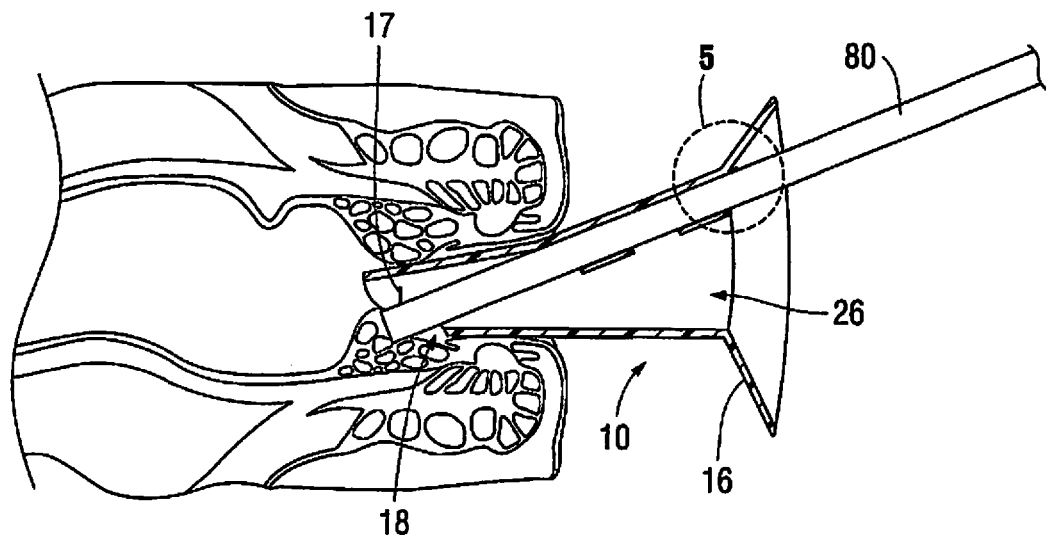
FIG. 4 is a cross-sectional view similar to FIG. 3B showing the ligation device of the present invention fully inserted through the anoscope.

As shown in FIG. 3A, channel 28 forms an acute angle with channel 26 and has a proximal opening 30 and a distal opening 32, the distal opening 32 communicating with channel 26 as it opens into channel 26 as shown for example in FIGS. 3A and 4. That is, channel 28 intersects channel 26 so an instrument inserted through channel 28 can extend into channel 26 to window 18 to access tissue through window 18. As discussed above and shown in the cross sectional views, wall 33 of anoscope 10 terminates at edge 22 distally of window 18 and opposing internal wall 31 terminates at edge 20 proximally of inner wall 33. Internal wall 35 of channel 28 terminates at edge 35a, preferably in an intermediate region of the anoscope 10.

Figure 2A:
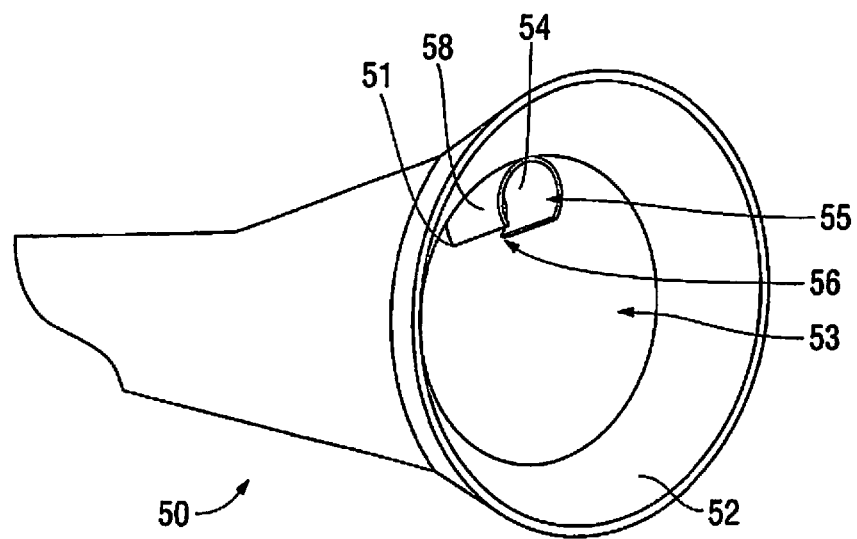
FIG. 2A is a front perspective view of an alternate embodiment of the anoscope of the present invention showing an internal channel open inferiorly.
Figure 2B:
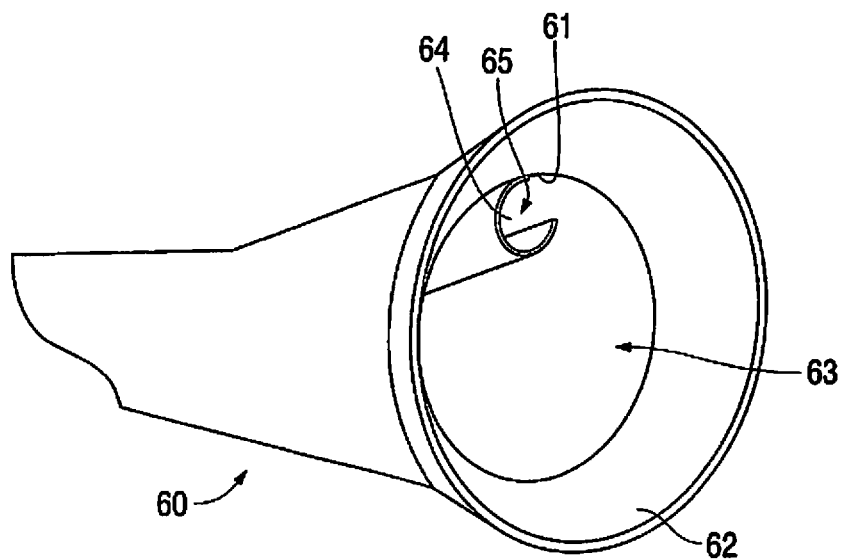
FIG. 2B is a front perspective view of an alternate embodiment of the anoscope of the present invention showing an internal channel open laterally.
Figure 2C:
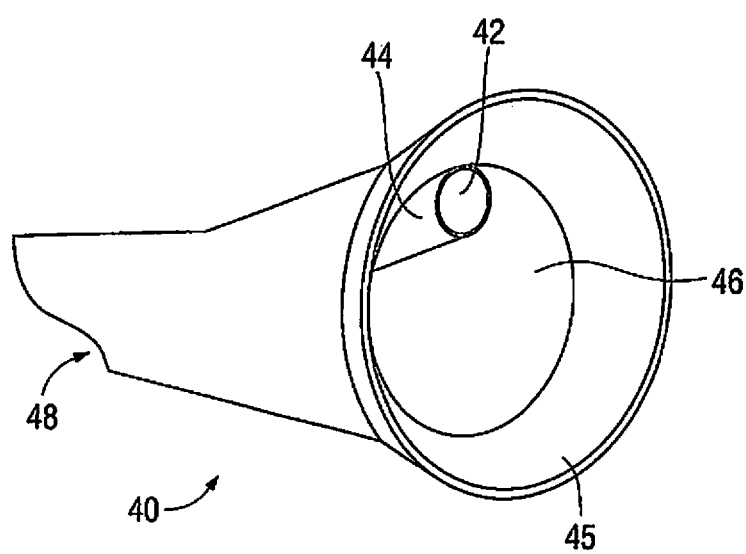
FIG. 2C is a front perspective view of another alternate embodiment of the anoscope of the present invention having a closed continuous channel.
Figure 3B:
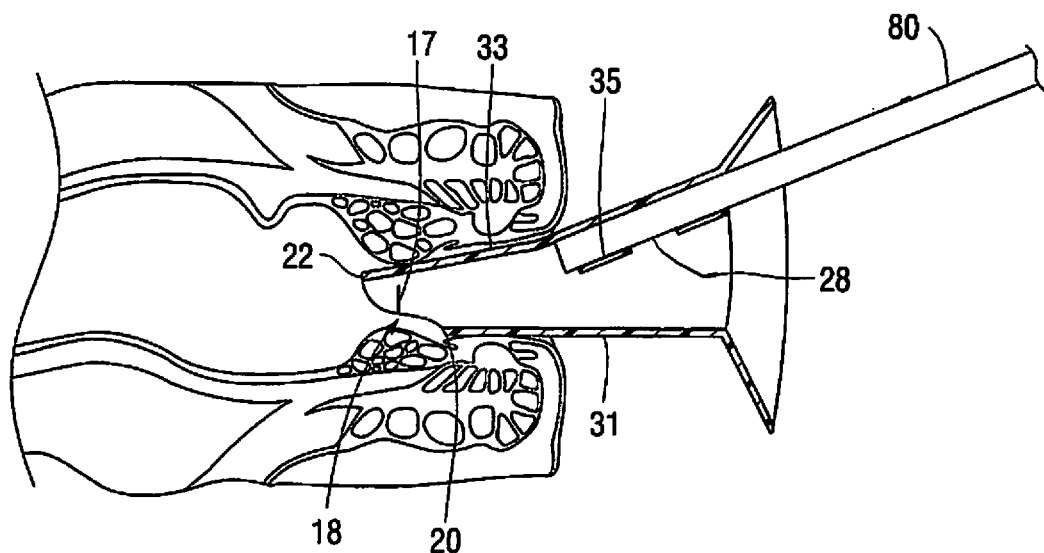
FIG. 3B is a cross-sectional view similar to FIG. 3A showing the ligation device of the present invention inserted through the channel of the anoscope of FIG. 1 (the obturator has been removed)
Figure 3C:
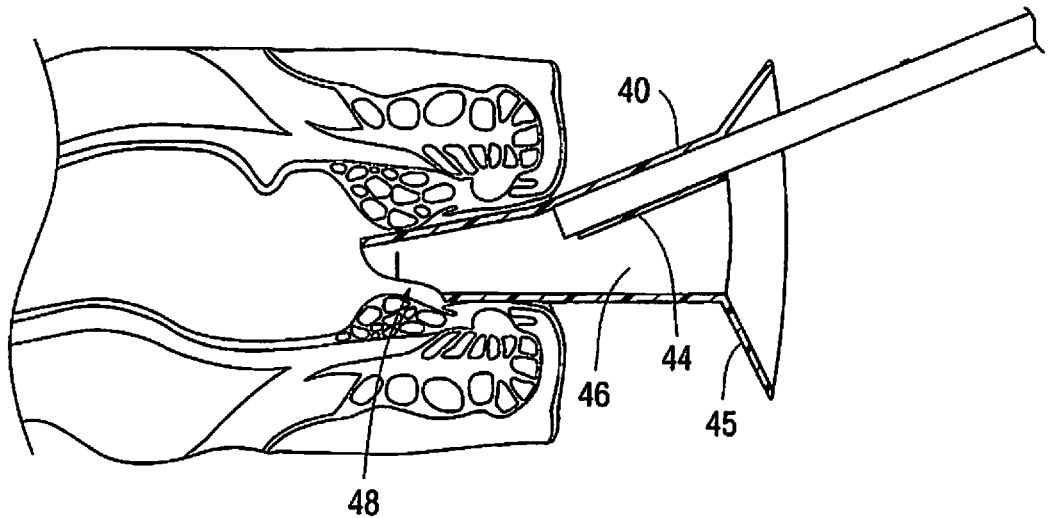
FIG. 3C is a cross-sectional view showing the ligation device of the present invention inserted through the channel of the anoscope of FIG. 2C (the obturator has been removed)

The internal wall of the instrument channel can be continuous along its length as shown in the alternate embodiment of FIGS. 2C and 3C. In this embodiment, a solid wall 44 forms the perimeter (circumference) of the instrument channel 42 of anoscope 40. The channel 42 can be of circular transverse cross-section, however, different shaped channels and different shaped cross-sections, e.g., oval, are also contemplated The anoscope 40 is otherwise identical to anoscope 10 and therefore for brevity will not be discussed in further detail since the structure and function of anoscope 10 is fully applicable to anoscope 40, i.e., the flange 45, main channel 46, window 48, etc.

Returning to the embodiment shown in FIGS. 1 and 3A, the internal wall 35 of channel 28, i.e., the wall facing the longitudinal axis of the channel 26, is a broken wall wherein the internal wall 35 has one or more gaps or fenestrations (openings) 37. This can be formed by forming gaps or openings in one or more regions of the wall 35, extending radially around a partial circumference of the wall of the channel 28. Alternatively, two or more shorter discrete channels can be provided, spaced apart axially, thereby providing an instrument channel with a non-continuous wall due to the space between the separated channels. Thus, instead of one or more partial circumferential fenestrations along a length, a full 360 degree gap(s) can be provided. This non-continuous wall (formed by fenestrations or separated channels), if utilized instead of a continuous wall, has the advantage of providing a relatively longer channel while reducing the amount of material as compared to if a long continuous channel wall is utilized. It could also simplify manufacture. Additionally, the gaps/openings in the wall enable the clinician to visualize the passage of the instrument through the instrument channel 28 as the clinician looks through the main channel 26 of the anoscope 10.

In the illustrated embodiment, the proximal opening 30 of channel 28 is within channel 26, just distal of flange 16, however, in alternate embodiments, the proximal opening 30 can be, i.e., the angled channel 28 can begin, within the flange 16 so it is more proximal than that shown in FIG. 3A or can begin at the proximal opening of the flange 16. Alternatively, the angled channel 28 can have a proximal opening distal of the position of FIG. 3A, e.g., distal of the distal end of the region of the flange 16. The angled inner wall 35 of the channel 28 preferably terminates in a mid region of the anoscope, leaving enough space so as not to interfere with insertion of obturator 70 as shown in FIG. 3A nor interfere with the clinician's naked eye viewing through channel 28. Note the wall 35 forming the wall of channel 28 can be of different lengths than that shown as long as it is of sufficient length to support an instrument and not excessive length so as to interfere with the obturator or obstruct the clinician's view through channel 26 of the anoscope. As mentioned above, the internal wall 35 can be a solid wall or alternatively can be a fully broken wall or a wall with fenestrations. Also note that the wall of the instrument channel 28 can be formed in part by the wall of the anoscope so that channel 28 and anoscope 10 share a common wall.

In the embodiment of FIG. 1, the outer wall 33 angles to intermediate region, i.e., angles inwardly toward the longitudinal axis of the anoscope, and then has a reduced angle toward the distal end while the opposing wall 31 (the wall of the window 18) is substantially linear, i.e., substantially aligned with the longitudinal axis. Alternatively, wall 31 can also be angled, e.g., angled inwardly toward the longitudinal axis. Tapers other than those illustrated are also contemplated.

FIGS. 2A and 2B illustrate alternate embodiments of the instrument channel of the anoscope of the present invention. Except for the instrument channels, the anoscope of FIG. 2A and FIG. 2B are identical to anoscope 10 of FIG. 1. Therefore the discussion of the anoscope (other than the instrument channels) is not repeated herein and only the instrument channels are discussed in detail since the other features and functions of anoscope 10, e.g., the flange, main channel, window, etc., are fully applicable to the anoscopes of FIGS. 2A and 2B.

Figure 3D:
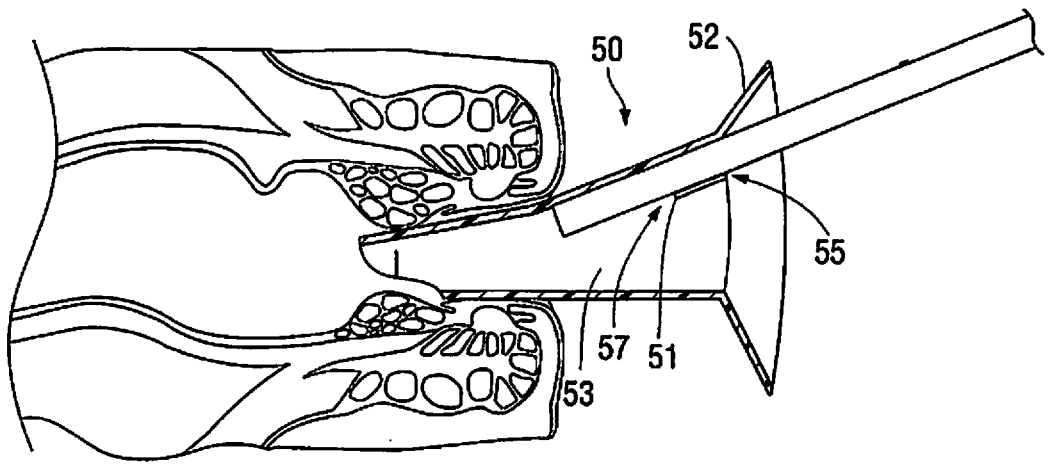
FIG. 3D is a cross-sectional view showing the ligation device of the present invention inserted through the channel of the anoscope of FIG. 2A (the obturator has been removed)

In FIG. 2A, the anoscope 50 has a proximal flange 52, a main channel 53 to removably receive an obturator, e.g., obturator 70, and an internal instrument channel 54. Instrument channel 54 has a partial wall segment as it opens inferiorly along its length. That is, channel 54 has a longitudinally extending elongated opening 56 extending along its length, with the elongated opening 56 facing the main channel 53 of the anoscope 50. Stated another way, the channel 54 is C or U-shaped as the circumference of its wall extends for less than 360 degrees. Channel 54 has a proximal opening 55 and a distal opening 57 (see FIG. 3D showing a cross-sectional view of the anoscope of FIG. 2A). As illustrated, the channel 54 is relatively short, extending for a minimal distance within the anoscope and terminating at distal end 51 a short distance from the flange 52. However, it should be appreciated that the channel 54 can be of a longer length such as the length of channel 28 of FIG. 3A.

The longitudinal opening 56 enables an instrument, e.g., a ligating instrument, to be loaded laterally into the channel 54. Such lateral loading is shown for example in FIGS. 16 and 17. This lateral insertion can be advantageous for example if the instrument is dimensioned so that it has regions of varying diameter which could not fit through proximal opening 55. In other words, if an instrument, such as a ligating instrument, has for example a distal region which has a diameter greater than a diameter of the channel 54, e.g., the diameter of the proximal opening 55, the instrument could not be inserted longitudinally through the opening 55 because it would not fit. However, it could be loaded into the channel 54 by inserting a smaller diameter portion laterally through the longitudinal opening 56 as shown. Clearly, if the instruments are of a small enough dimension, rather than lateral insertion, if desired, they can alternatively be inserted into the channel 54 through proximal opening 55 such as shown in FIG. 18. Thus, channel 54 allows for both proximal (longitudinal) and lateral insertion of the instrument therein, which can be dependent on the size of the instrument utilized. Additionally, it in certain embodiments, the channel 54 can be made of a material that is flexible so that the instrument could have a slightly larger diameter which flexes the channel 54 (walls of the channel) as it is inserted laterally therein. That is, the wall 58 of the instrument channel can be composed of a material that provides sufficient flexibility to expand when the instrument is inserted laterally (and also longitudinally). This would enable larger instruments to be laterally inserted therein as the instrument would flex the wall of the channel 54 to widen the longitudinal opening 56 for insertion, and then after insertion the wall would flex back toward a more closed position. Sufficient flexibility could also allow a larger diameter instrument to be inserted longitudinally since the elongated opening increases the flexibility of the instrument channel.

The shorter channel if utilized provides the advantages enumerated above of less material and improved visualization of the instrument by the clinician as it is being inserted through the channel 54 since minimal part of the instrument is blocked by the wall of the channel.

Figure 16:
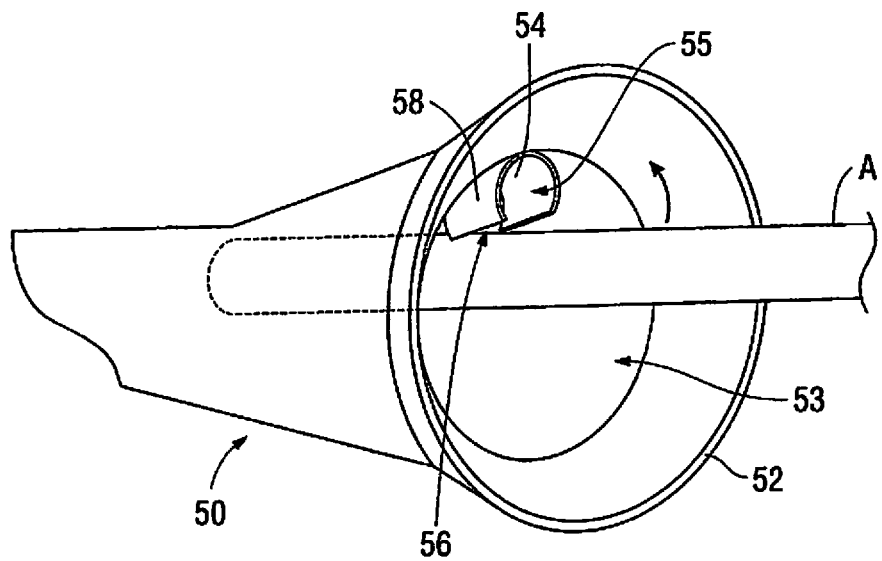
FIGS. 16 and 17 are perspective views showing the ligation device inserted laterally into the internal channel of the anoscope of FIG. 2A.
Figure 17:
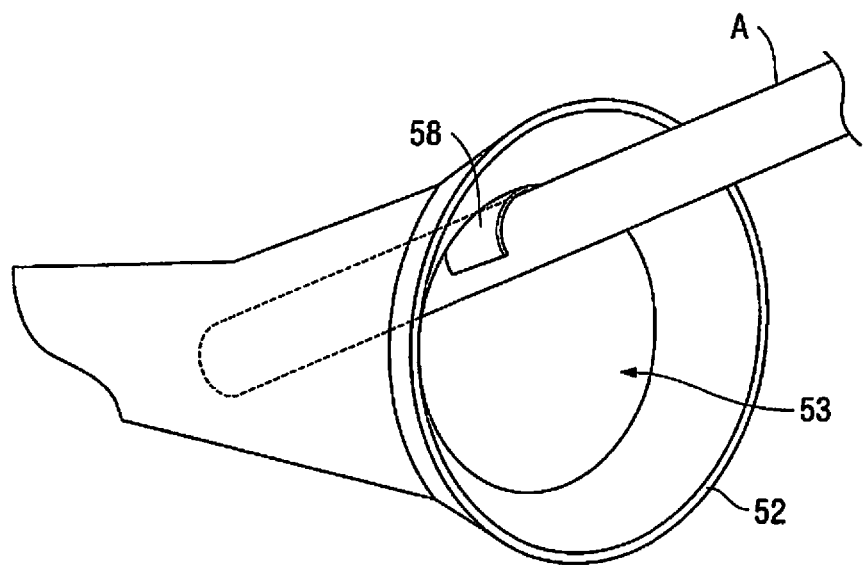
Figure 18:
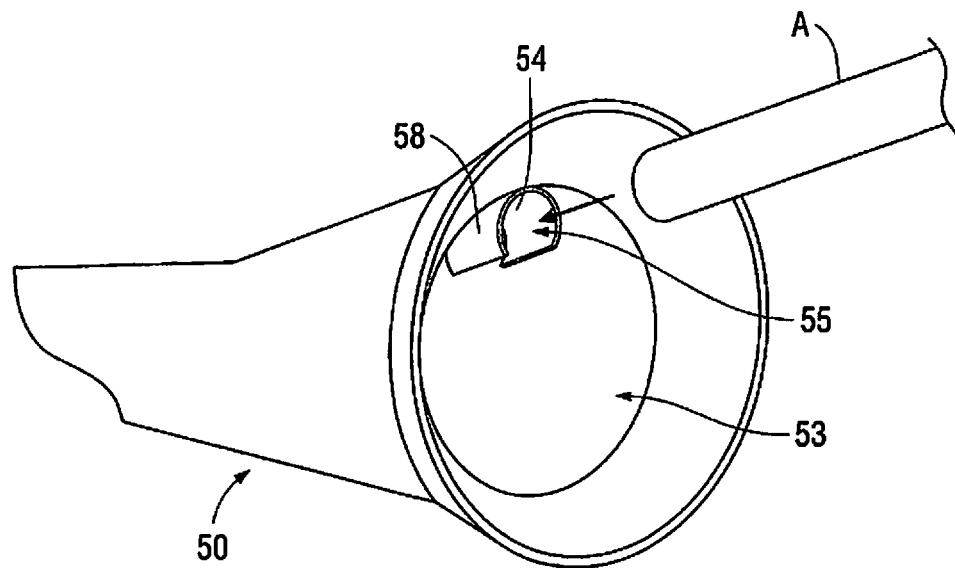
FIG. 18 is a perspective view showing the ligation device inserted longitudinally through the proximal opening of the internal channel of the anoscope of FIG. 2A

Note in FIGS. 16 and 17 (and 18) the instrument is shown schematically and labeled as instrument A as various types and sizes of instruments, including the ligating instrument of the present disclosure, can be utilized with the anoscope 10

An alternate embodiment of the instrument channel is illustrated in FIG. 2B. In this embodiment, the internal instrument channel 64 of anoscope 60 has an opening 65 along its length which rather than facing inferiorly, faces in another lateral direction. Anoscope 60, like anoscope 10, has a proximal flange 62 and a main channel 63 to removably receive an obturator, e.g., obturator 70. Instrument channel 64 has a partial wall segment as it opens along its length, facing away from the longitudinal axis of anoscope 60 and toward wall 61 of anoscope 60. The channel 64 is C or U-shaped as the circumference of its wall extends for less than 360 degrees. Channel 64 has a proximal opening 65 and a distal opening. As illustrated, the channel 64 is longer than channel 54 as it extends further into the anoscope 10, for example a distance of the instrument channel of FIG. 3C. Alternatively, it could be relatively short, extending for a minimal distance within the anoscope and terminating at a distal end a short distance from the flange 62 in the same manner as channel 54 of anoscope 50 of FIGS. 2A and 3D. In either length, the elongated longitudinally extending opening 65 enables an instrument, e.g., a ligating instrument, to be loaded laterally into the channel 64 as in the lateral loading shown in FIGS. 16 and 17, however, the approach to the channel 64 would be different since the longitudinal opening is at a different region than the opening 56 in channel 54. Loading longitudinally through the proximal opening 65 as in FIG. 18 is also contemplated if the instrument size permits. The lateral insertion can be advantageous for the reasons described above. Advantages of a shorter channel are also described above. However, it should be appreciated that the longer channel has the advantage of improved stability of the instrument positioned therein because the instrument is retained along a longer length. As with channel 54, in certain embodiments, the channel 64 can be made of a material that is flexible so that the instrument could have a slightly larger diameter which flexes the channel 64 as it is inserted laterally therein or even if inserted longitudinally through the proximal opening 65, and then after insertion the wall would flex back toward a more closed position.

FIGS. 2A and 2B show examples of positioning of the longitudinal opening with respect to the main channel of the endoscope. It should be appreciated, that the openings could be located in other positions. Also, the openings can be of larger or smaller size. For example, the channel can have an opening in the form of a narrow slit extending along its length.

Thus, the asymmetric anoscope 10 of the present invention, in the embodiments described herein, has a dedicated channel on the wall opposite to the target tissue to receive an instrument (device) such as the rubber band ligator (also referred to herein as an elastic band ligator) to form a guide section. The channel can be in the shape of a cylinder (or alternatively other configurations), which can have a separate wall or share the wall with the anoscope and/or have a continuous or non-continuous, e.g., a fenestrated wall. A single channel forming the guide section can be provided or alternatively two or more axial spaced channels can provide guiding sections for the instrument, e.g., the ligator, through the anoscope. The channel can also have a longitudinal slot or opening along its length, providing a cross-sectional configuration of a C or U shape.

The anoscope of any of the embodiments disclosed herein can include a visual marker such as red marker on the exterior and/or interior side wall of the anoscope by the treatment window, although other markers/indicators are also contemplated. Such marker is shown for example in FIG. 3B and designated by reference numeral 17. The marker 17 is located between walls 33 and 31 and the distal edges 22 and 20. The marker aids the positioning of the anoscope relative to the dentate line. That is, the anoscopes disclosed herein are positioned so that the dentate line of the patient is visible just anatomically proximal to the proximal edge of the treatment window of the anoscope—the target point for tissue ligation. Therefore, the anoscope is positioned so the marker 17 is aligned with the target tissue and approximately 2 cm from the dentate line. This means the anoscope is inserted so the marker 17 is approximately 7 cm from the anal orifice.

Figure 5:
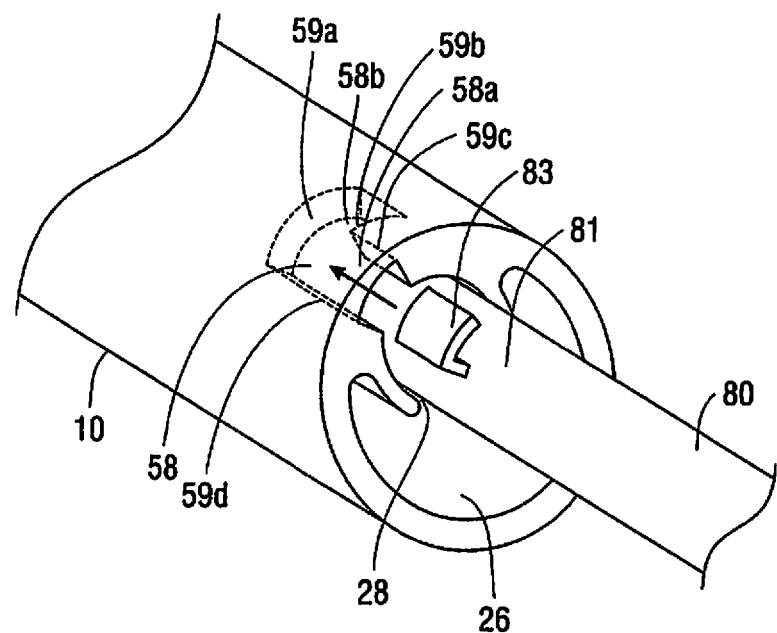
FIG. 5 is a close-up view of the area of detail identified in FIG. 4 showing the ligation device inserted through the channel of the anoscope of FIG. 2A prior to engagement with the stop/lockout.
Figure 6:
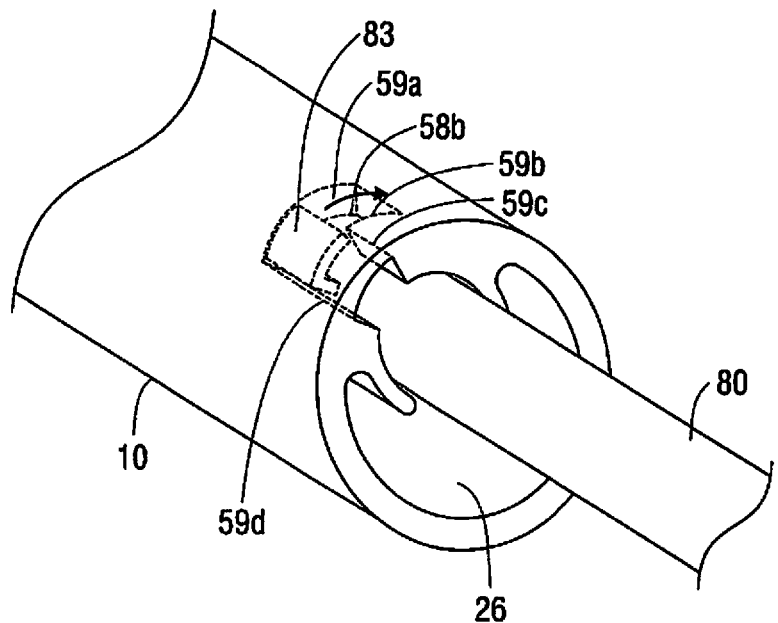
FIG. 6 is a view similar to FIG. 5 showing the ligation device further inserted through the channel to engage the distal stop and align with the radial slot, the arrow indicating the rotational movement of the ligation device.
Figure 7:
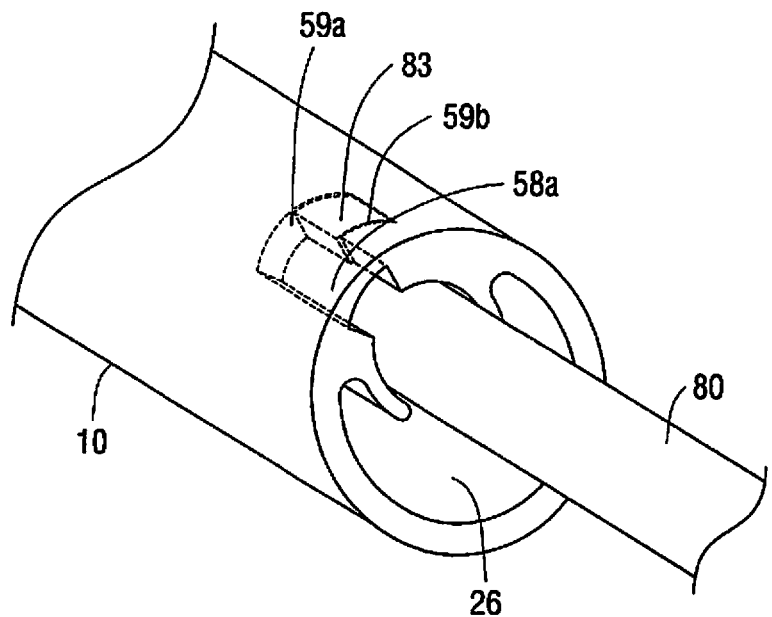
FIG. 7 is a view similar to FIG. 6 showing the ligation device rotated within the channel to engage the proximal stop and interlock with the anoscope to restrict axial movement.

The anoscope of any of the embodiments disclosed herein can include a structure to engage, e.g., interlock, with the ligating instrument to restrict movement of the ligating instrument with respect to the anoscope. Such structure, which is also referred to herein as a locking structure, interlocking structure or a blocking structure, is shown in FIGS. 5, 6 and 7. Anoscope 50 is illustrated by way of example to illustrate the locking structure, it being understood that the other anoscopes disclosed herein can also have this locking structure. As shown in FIG. 5, anoscope 10 has a slot 58 formed in its wall, the slot 58 having an axial region 58a and a radial region 58b, forming an L-shape, the radial region being a more distal region. The slot 58 can be located at a proximal end of the anoscope 50, e.g., just distal of the flange 52 as shown by the designated area of detail of FIG. 4. Alternatively, it can be located at other regions of the anoscope, e.g., further distal than the location of FIG. 4.

Slot 58 has a distal wall 59a at the distal end of axial region 58a that forms a distal stop for the ligating instrument. Radial region 58b has a proximal wall 59b forming a proximal stop for the ligating instrument. Radial region 58b shares the distal wall 59a. The distal stop restricts distal movement of the ligating instrument within the anoscope and the proximal stop restricts proximal movement of the ligating instrument within the anoscope. The ligating instrument 80 has engagement structure 83 extending from an outer surface 81 of its outer wall which can be in the form of a hook-like engagement member. When the ligating instrument 80 is initially inserted into channel 54 of anoscope 50, engagement structure 83 is received in the narrower axial slot region 58*a* and the ligating instrument 80 cannot rotate in either direction as it is blocked by side walls 59*c* and 59*d* of slot region 58*a*. When the ligating, instrument 80 is advanced, its engagement structure 83 contacts distal wall 59*a*. Thus, distal wall 59*a* restricts (blocks) further distal movement of the ligating instrument 80. At this point when the distal stop surface (wall 59*a*) is engaged by engagement structure 83 of ligating instrument 80, the engagement structure 83 of the ligating instrument 80 is aligned with the radial slot region 58*b* as shown in FIG. 6. This slot region 58*b* provides room for the ligating instrument 80 to be rotated in the direction of the arrow of FIG. 6 to the position of FIG. 7. In this position of FIG. 7, the ligating instrument 80 still cannot be advanced distally due to wall 59*a* and further cannot be retracted proximally due to proximal wall 59*b*. Thus, the distal and proximal walls of the engagement structure 83 abut the respective distal and proximal walls 59*a*, 59*b* to prevent axial movement in either direction. This maintains the ligating instrument 80 in its axial position during the procedure, ensuring that its position with respect to the dentate line (and marker on the anoscope if provided) is maintained during the surgical procedure. Note that to remove the instrument after the procedure, the ligating instrument 80 is rotated in the opposite direction of the arrow of FIG. 6 to re-align the engagement structure 83 of the ligating instrument 80 with the axial slot region 58*a* so it can be withdrawn proximally along the region 58*a*.

Thus, the anoscope 50 has a channel or slot to receive a raised portion (raised engagement or locking structure) of the ligating instrument, with the channel having a first configuration and a second different configuration, The first configuration restricts rotation of the ligating device within the anoscope during its insertion distally and the second configuration allows slight rotation of the ligating device to enable engagement of the proximal stop to interlock the ligating instrument and anoscope to restrict proximal and distal axial movement of the ligating instrument within the instrument channel. Thus, the ligating device is first stopped by the stopping feature and subsequently locked by the device's locking feature so the tip of the ligating instrument 80 is placed and fixated at the target tissue (cross of the line corresponding to the device marker and a line corresponding to the middle of the lower wall of the anoscope). Although described above for locking ligating instrument 80, other instruments can be provided with the engagement structure to provide for locking to the anoscope in the manner described herein.

Note during insertion through the axial slot region 58*a*, as noted above, the ligating instrument cannot be rotated. However, when in the radial slot region 58*b*, it can be rotated back into alignment with slot region 58*a*. To limit rotation during the procedure when it is engaged with the radial region 58*b*, the proximal wall 59*b* and/or the distal wall 59*a* in the region of slot region 58*b* can be provided with one or more detents or other structure so that a predetermined force is required to rotate the ligating instrument and engagement structure from the position of FIG. 7 back to the position of FIG. 6. In this manner, rotational movement of the ligating instrument can be restricted unless the clinician rotates the ligating instrument with a sufficient force to override the detent(s) to align with axial slot region 58*a*. With this provision, the ligating instrument would be locked (blocked) from axial and rotational movement during use.

It should also be appreciated that due to the engagement structure/slot arrangement in this embodiment, the ligating instrument can only be inserted in an orientation where the engagement structure is aligned with the slot. If not aligned, the instrument will not fit within the channel. To facilitate such orientation, one or more markers can be provided on the anoscope to aid alignment of the ligating instrument with the slotted region of the anoscope.

Figure 8A:
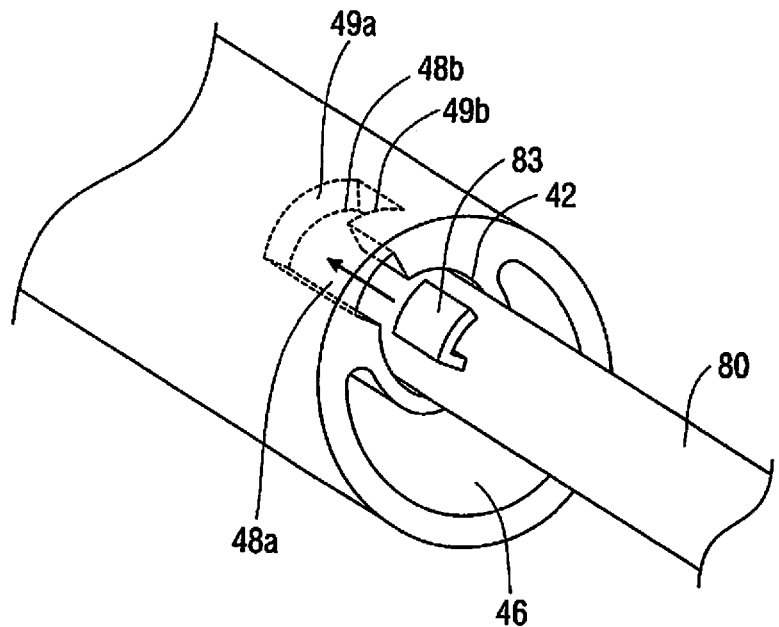
FIG. 8A is a view similar to FIG. 5 showing the ligation device inserted through the channel of the anoscope of FIG. 2C prior to engagement with the stop/lockout.

FIGS. 5-7 show the slot regions 58*a*, 58*b* formed in the anoscope 50 of FIG. 3A. By way of another example, FIG. 8A shows such slotted regions used with the anoscope 40 of FIG. 2C having a closed channel 42. The slot regions 48*a*, 48*b* of FIG. 8A are identical to the slot regions 58*a*, 58*b*, respectively, of FIGS. 5-7 and therefore further discussion is not warranted since the interaction of the ligating instrument 80 with the slot regions 58*a*, 58*b* and distal and proximal walls 59*a*, 59*b* is fully applicable to the slot regions 48*a*, 48*b* and distal and proximal walls 49*a*, 49*b* of anoscope 40. The interaction with anoscope 40 is shown to illustrate by way of example that the interlocking structure can be utilized with any of the instrument channels disclosed herein.

FIGS. 5-8A illustrate one type of stop and locking mechanism. It is also contemplated that other mechanisms can be provided to restrict distal advancement of the instrument through the channel of the anoscope and/or lock axial movement in both proximal and distal directions and/or restrict rotation of the instrument with respect to the anoscope.

Figure 9:
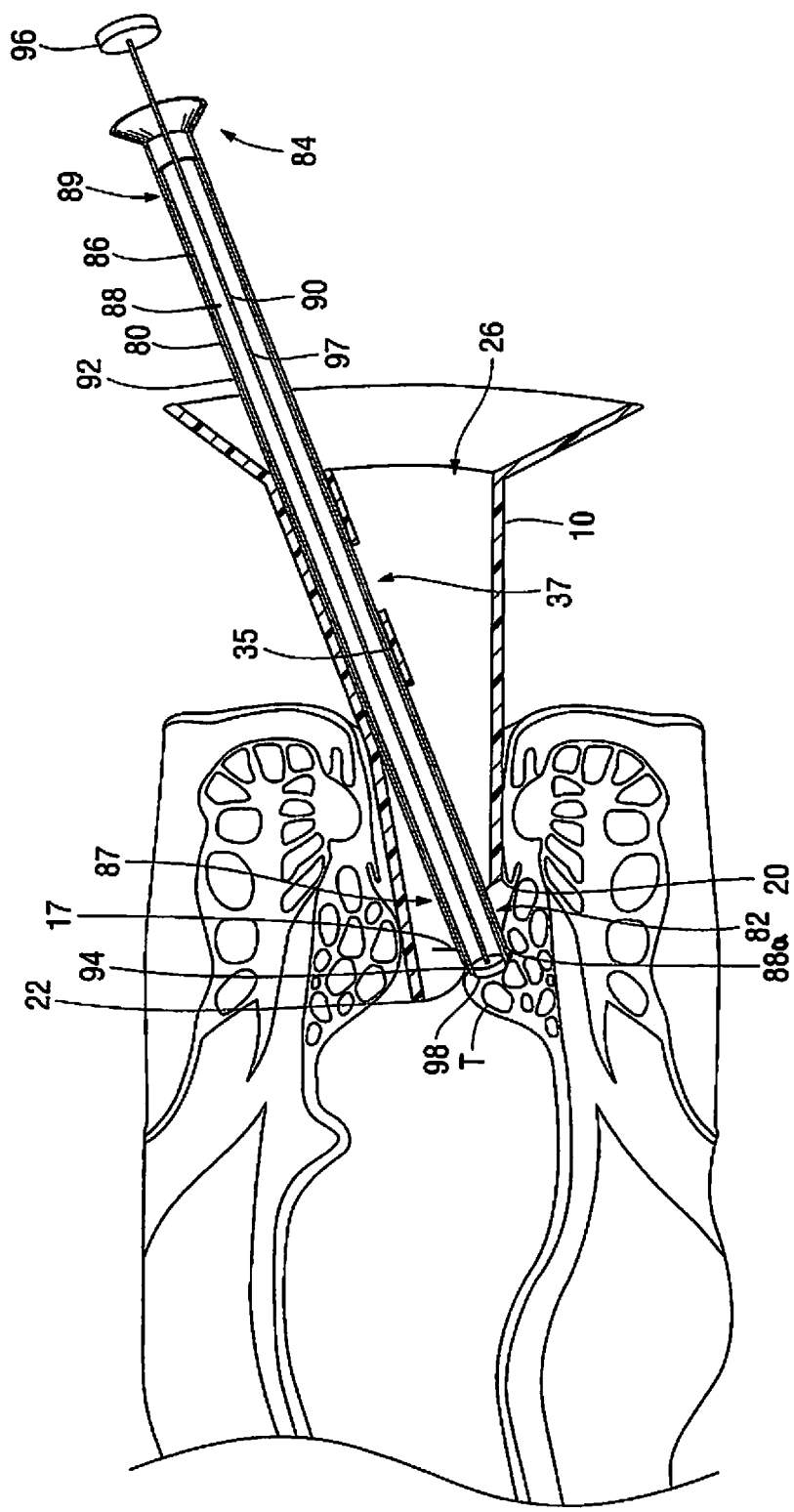
FIG. 9 is a cross-sectional view showing the ligation device extending through the anoscope of FIG. 1 and showing the inner tube and plunger plate engaged with the hemorrhoid tissue.

Turning now to the rubber (elastic) band ligation device (also referred to herein as the ligator or ligating device or ligating instrument) of the present invention, and with initial reference to FIG. 9 which shows the ligating device already inserted through the anoscope, ligating device (instrument) 80 has a distal portion 82 for positioning within the body of the patient and a proximal portion 84 extending outside the body for manipulation by the operator (clinician). Ligating device 80 includes an inner or middle tube-like structure 86 with a lumen (channel) 88, a plunger 90 slidable within lumen 88 of inner tube 86 and an outer tube 92 with a lumen (channel) to receive the inner tube 86. The inner and outer tubes 86, 92 are relatively movable. The plunger 90 and inner tube 86 are also relatively movable. An elastic (rubber) band 94 is carried, e.g., supported in tension, by the inner tube 86 and is positioned on an exterior wall 88*a* of the inner tube 86 for deployment therefrom by distal advancement of the outer tube 92 which pushes the elastic band 94 off wall 88*a*. The inner tube 86 has a distal end 87 and proximal end 89. The distal end is 87 substantially round or oval, although other configurations are contemplated, and engages the target tissue to work with the plunger 90 for suctioning tissue. The proximal end 89 extends proximally of the anoscope. The wall of inner tube 86 and outer tube 92 may be whole or incomplete, e.g., have fenestrations, to reduce the amount of material and to enable viewing of the plunger 90 sliding within the lumen 88 of the inner tube 86.

Figure 8B:
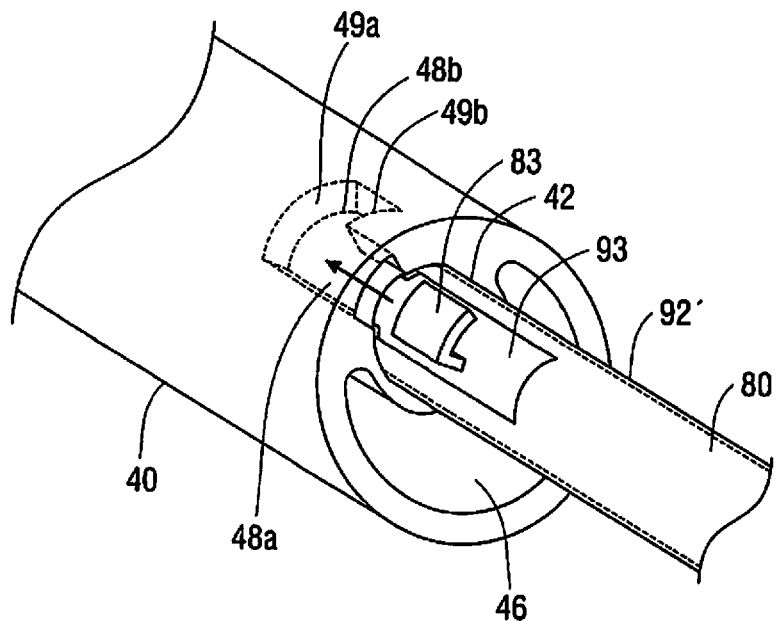
FIG. 8B is a view similar to FIG. 8A showing the outer tube with a window.

The proximal end 89 of the inner tube 86 can extend proximally of the outer tube 92 or the proximal end alternatively can terminate distally of the proximal end of the outer tube 92. The inner tube 86 can contain the projecting engagement structure 83 which releasably engages the stopping and locking features at a proximal end of the anoscope. A portion of the outer tube 92 can be cut away to expose the engagement structure 83 of inner tube 86 so that the engagement structure 83 can interact with the slotted regions (e.g., regions 58*a*, 58*b*) of the anoscope to provide the aforedescribed axial and rotational restrictions. The outer tube 92 can alternatively have a circumference of less than 360 degrees, e.g., be C or U-shaped along its length, or partial length, to expose the engagement structure 83 or engagement with the slotted regions 58a and 58b. FIG. 8B illustrates by way of example an embodiment of the outer tube 92' having a window or cutout 93 formed therein aligned with the engagement structure 83 of inner tube 86. The window 93 exposes the engagement structure 83. The window 93 allows for sufficient longitudinal (axial) movement of the outer tube 92' with respect to the inner tube 86 to dislodge a rubber band from the ligating instrument 80. The outer tube 92' with window 93 can be utilized with any of the embodiments of the ligating instrument and anoscope disclosed herein and is shown in conjunction with the anoscope 40 of FIG. 8A by way of example.

Note in alternate embodiments, the projecting engagement structure can be located on the outer tube 92 and the inner tube 86 and outer tube 92 would be interlocked so that stopping and locking of the outer tube 92 to prevent axial and/or rotational movement, would likewise result in stopping and locking the inner tube 86 as well.

Referring back to FIG. 9, the plunger 90 includes a proximal handle 96 for gripping by the user, an elongated rod 97 extending distally from the handle 96, and a transversely (horizontally) extending plate 98 connected at the distal end of rod 97. The handle 96 extends proximally of the inner tube 86 and outside the patient for access by the clinician. The rod 97 can be connected to an upper (proximal) surface of the plate 98, and can in some embodiments be connected to a central region of the plate 98. The plate 98 can be round, oval or other configurations. The plunger 90 provides for suctioning of the tissue into the inner tube 86 for subsequent application of the elastic band.

One of the main technical challenges for an operator during the rubber band ligation technique is related to the need, while holding the anoscope, to pull on the target tissue and when "just the right amount" of the target tissue appears to be engaged, to release the rubber band onto the base of the pulled tissue. These maneuvers require coordinated manipulations of both hands of the operator and possibly an assistant holding the anoscope. In addition, the view of the target area can be obscured by the instruments and the operator's own hands, further challenging the procedure. Also, the amount of the suctioned tissue may need to vary from case to case and in certain instances, e.g., if more than the desired amount of tissue is suctioned into the inner tube, the need might exist to "slightly release" the suctioned tissue.

The plunger 90 slides within the inner (middle) tube-like structure 86. The plate 98 of the plunger 90 is positioned distally of the inner tube 86. Such distal positioning can be achieved during use or alternatively, the instrument can be provided so that the plate 98 is always located distally, i.e., during packaging, initial insertion and use.

The plunger 90 is actuated by the operator's hand for the purpose of creating and gauging the suction on the target tissue. By moving the plunger 90 forward (distally) towards the target tissue, the tissue can be engaged. By moving the plunger backward (proximally) while the distal end of the inner (middle) tube 86 is hermetically pressed against the target area, the target tissue is suctioned into the distal end (the target tissue chamber) of the inner tube 86. The inner tube 86 thus forms a target tissue chamber within its lumen 88 for receipt of the suctioned tissue. If excess tissue is suctioned into the inner tube 86, the clinician can re-advance the plunger 90 as in FIG. 11 to release the suction and thereby release some of the tissue. Thus, such distal movement enables the user to release a portion of the suctioned tissue or, if desired, release the entire suctioned tissue from the tissue chamber formed in the inner tube 86.

Figure 19:
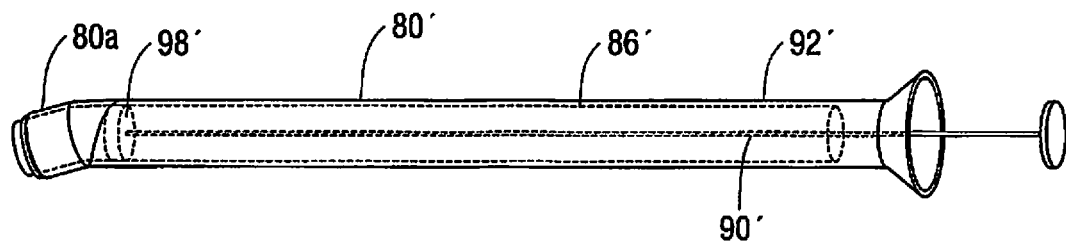
FIG. 19 is a side perspective view of an alternate embodiment of the ligation device of the present invention having a bent distal tip.

FIG. 19 illustrates an alternate embodiment of the ligating device of the present invention. The ligating device 80' is identical to ligating device 80 of FIG. 9 except that it has a bent distal tip 80a. The bent tip 80a is bent toward the target tissue and in certain applications might facilitate tissue engagement and might improve access and visibility of the target tissue. Device 80' is otherwise identical to device 80 so for brevity is not further discussed since the structure and function of device 80 are fully applicable to device 80'. For ease of understanding, the like (corresponding) components of device 80' have been designated with prime reference numerals, e.g., plunger 90', plate 98', inner tube 86', outer tube 92'. As with the device 80, device 80' can include a mechanism (actuator) to advance the inner tube or the inner tube can be accessible to the user at a proximal end extending proximally of the outer tube or through an opening in the outer tube that enables access to the inner tube.

Figure 20:
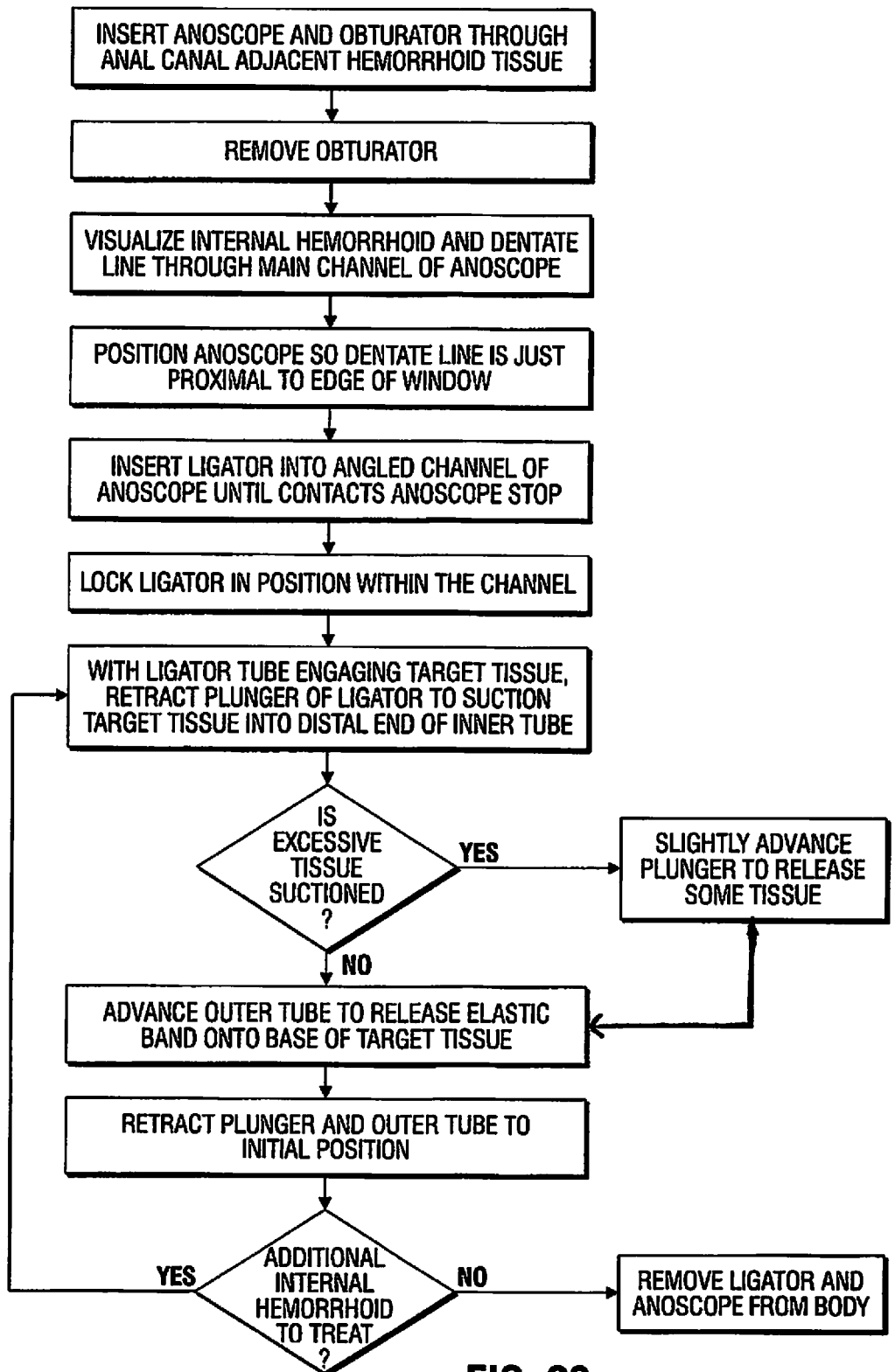
FIG. 20 is a flow chart depicting the steps of one embodiment of the method of the present invention.

The use of the anoscope and ligating device of the present invention will now be described, in conjunction with FIGS. 3A, 9-15 and the flow chart of FIG. 20. Note the discussion of the method of use is described with the use of anoscope 10, it being understood that the anoscope of the other embodiments disclosed herein could be utilized and would operate in a similar fashion, except for the possible lateral insertion of the ligating instrument into the instrument channel as described above rather than the longitudinal insertion. The ligating device described and illustrated in these Figures is the aforedescribed ligating device 80.

In the first step, the blunt tip obturator 70 is inserted longitudinally into the main channel 26 of the anoscope (cannula) 10 and then the anoscope (cannula) 10 with the blunt tip obturator 70 positioned therein and extending slightly distally of the anoscope 10 are introduced into the rectum of the patient, inserted approximately 7 cm into the rectum (see FIG. 3A). The obturator 70 is then removed from the anoscope and the internal hemorrhoid and dentate line are visualized through the proximal opening and channel 26 of the anoscope 10. The anoscope 10 is positioned so the marker 17 is spaced a predetermined distance from the dentate line, e.g., 2 cm anatomically proximal of the dentate line. Thus, in the illustrated embodiment, the edge 20 adjacent the window 18 of can be positioned at the dentate line (or just proximal of the dentate line) since the marker 17 is positioned 2 cm from the edge 20.

Next, with the position of the anoscope 10 satisfactory (via direct visualization), the ligating device (ligator) 80 is inserted into the angled channel (lumen) 28 of the anoscope (FIGS. 3B and 9) and moved forward towards the marker 17 which provides the identification of the target area. Lateral movement of the ligating device 80 is restricted by wall of the channel 28. The ligating device 80 is advanced until stopped by the device-stopping feature of FIGS. 5-7 as the projecting engagement structure 83 of the ligating device 80 contacts the distal wall 59a of the slot 58a of the anoscope 10. Note the ligating device 80 is aligned with the channel 28 so that its engagement surface 83 is aligned with slotted region 58a so it can slide within the channel 28. Note the ligating device 80 can be inserted into the channel 28 either longitudinally as in FIG. 18 or laterally as in FIG. 17. When in abutment with the stop (distal wall 59a), the tip of the device 80 is in the desired position with respect to the target hemorrhoid tissue T and the dentate line (FIG. 9). After contacting the distal stop, i.e., distal wall 59a, the ligating device 80 is rotated (FIGS. 6-7) so the engagement structure 83 moves into radial slot 58b, thereby locking the ligating device 80 as proximal and distal axial movement are restrained. In this locked position, the distal end of the ligating device 80 is engaged with the hemorrhoid tissue anatomically proximal of the patient's dentate line, thereby ensuring the elastic band is not placed too close to the dentate line which can lead to undesirable side effects/complications such as severe pain, tenesmus, fainting, rectal perforation, infection, and/or severe bleeding. With the ligating device 80 fixed to the anoscope 10, the operator visually confirms the desired target position.

Figure 10:
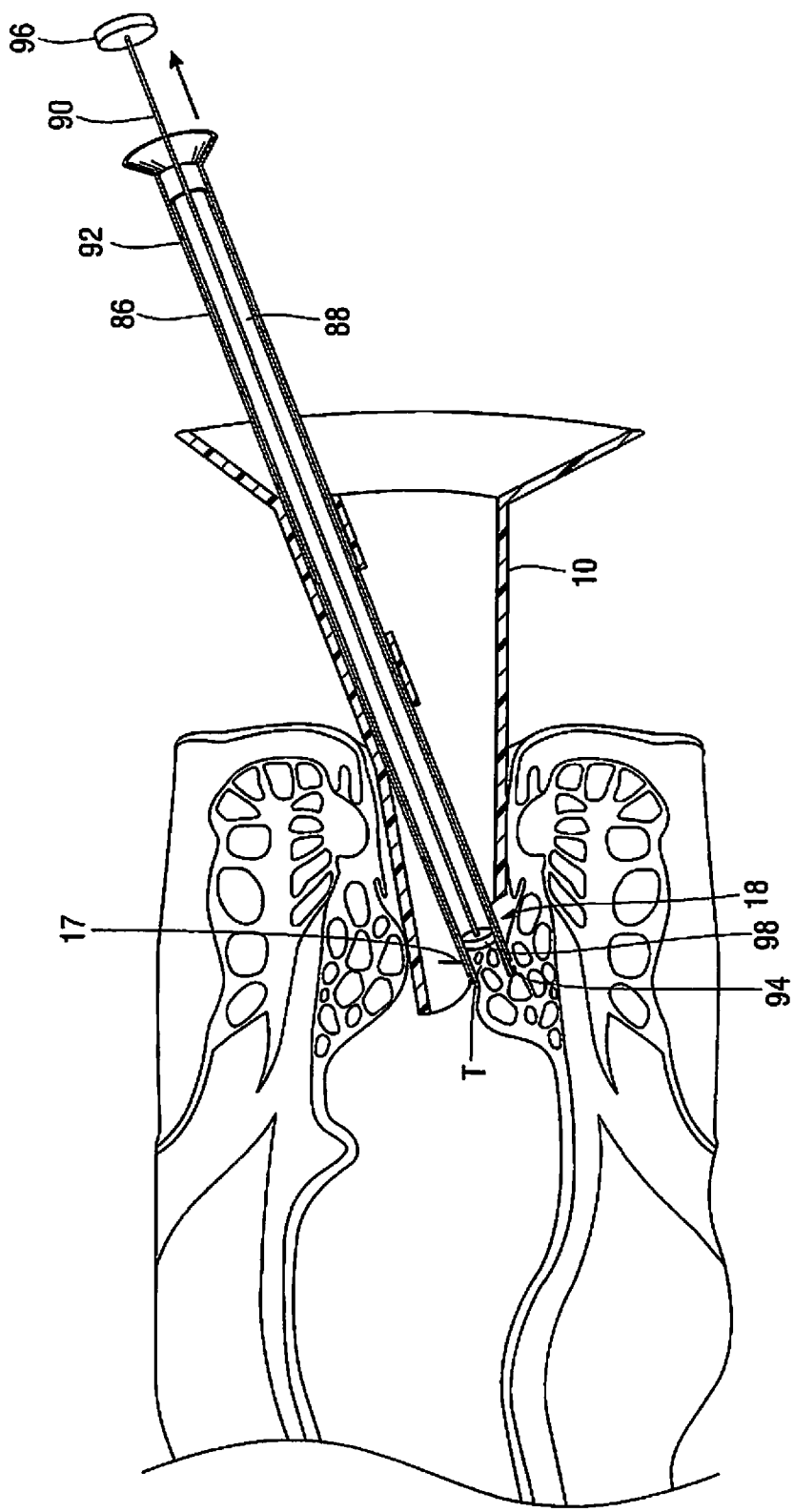
FIG. 10 is a view similar to FIG. 9 showing the plunger retracted to suction target tissue within the inner tube.
Figure 11:
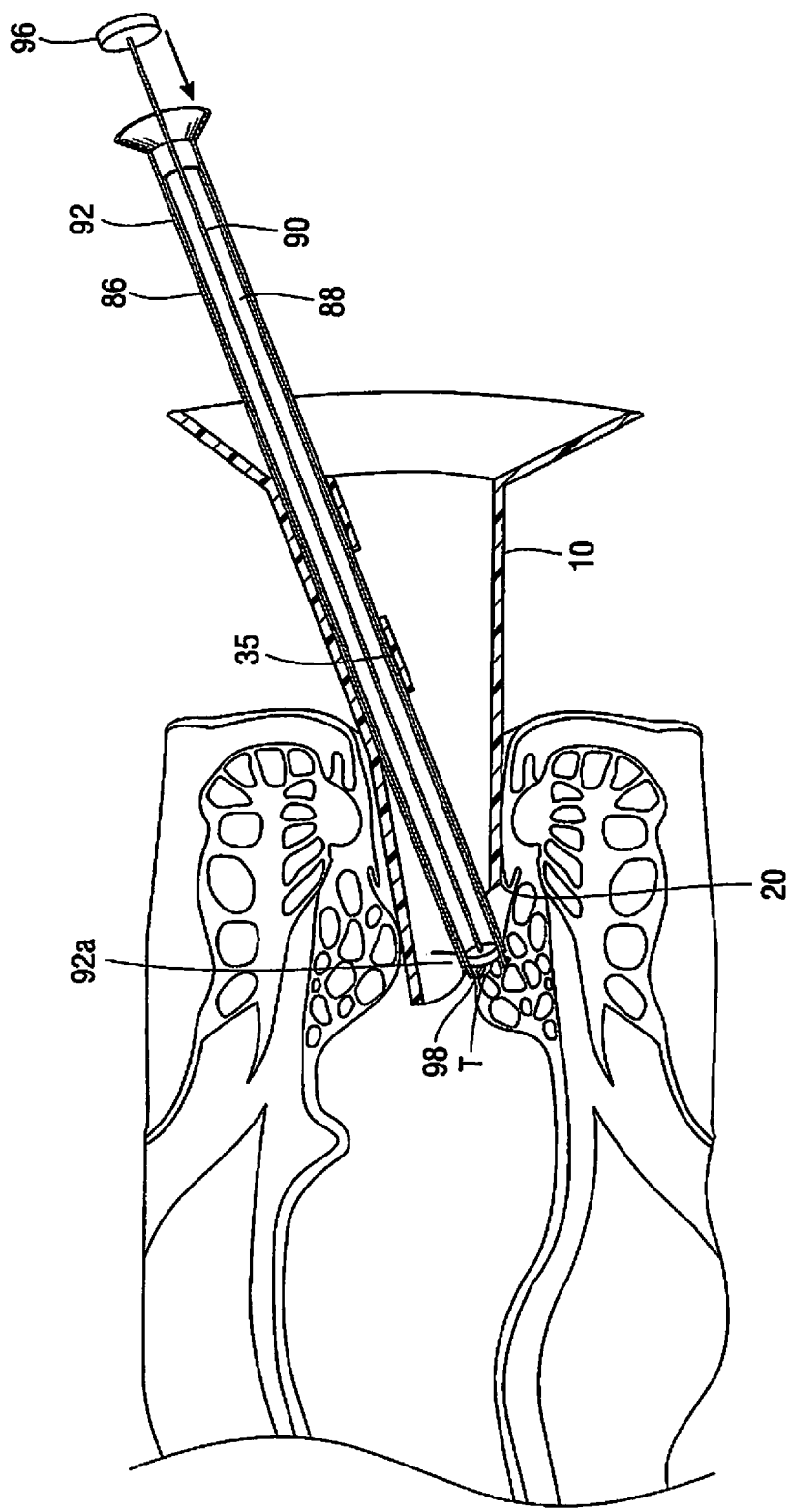
FIG. 11 is a view similar to FIG. 10 showing the plunger slightly advanced to release some of the suctioned tissue.

Once confirmed, the plunger 90 inside the hollow internal tube 86 is then slowly pulled back as the end of the inner tube 86 presses and seals against the tissue as shown in FIG. 10, thereby suctioning the target tissue into the lumen 88 of the inner tube 86 under direct visualization and assuring that the patient is not experiencing any discomfort. After the desired amount of the target tissue is suctioned into the distal chamber within the lumen 88, the elastic band 94 is ready to be applied. However, prior to elastic band application, if the operator determines that too much tissue has been suctioned into the chamber of the internal tube 88, the plunger 90 can be advanced distally as shown in FIG. 11 to release some of the tissue. Note that if it is desired to fully release the tissue to then re-suction the tissue from the beginning, the plunger 90 can be pushed distally to its original position, thereby entirely releasing the suction. Also note that if the operator is satisfied with the amount of tissue suctioned into the chamber of the inner tube 86, then the step of FIG. 11 is omitted and the operator proceeds to the elastic rubber band application as in FIG. 12. This is illustrated in the flow chart of FIG. 20 at the decision box inquiring whether excessive tissue has been suctioned.

Figure 12:
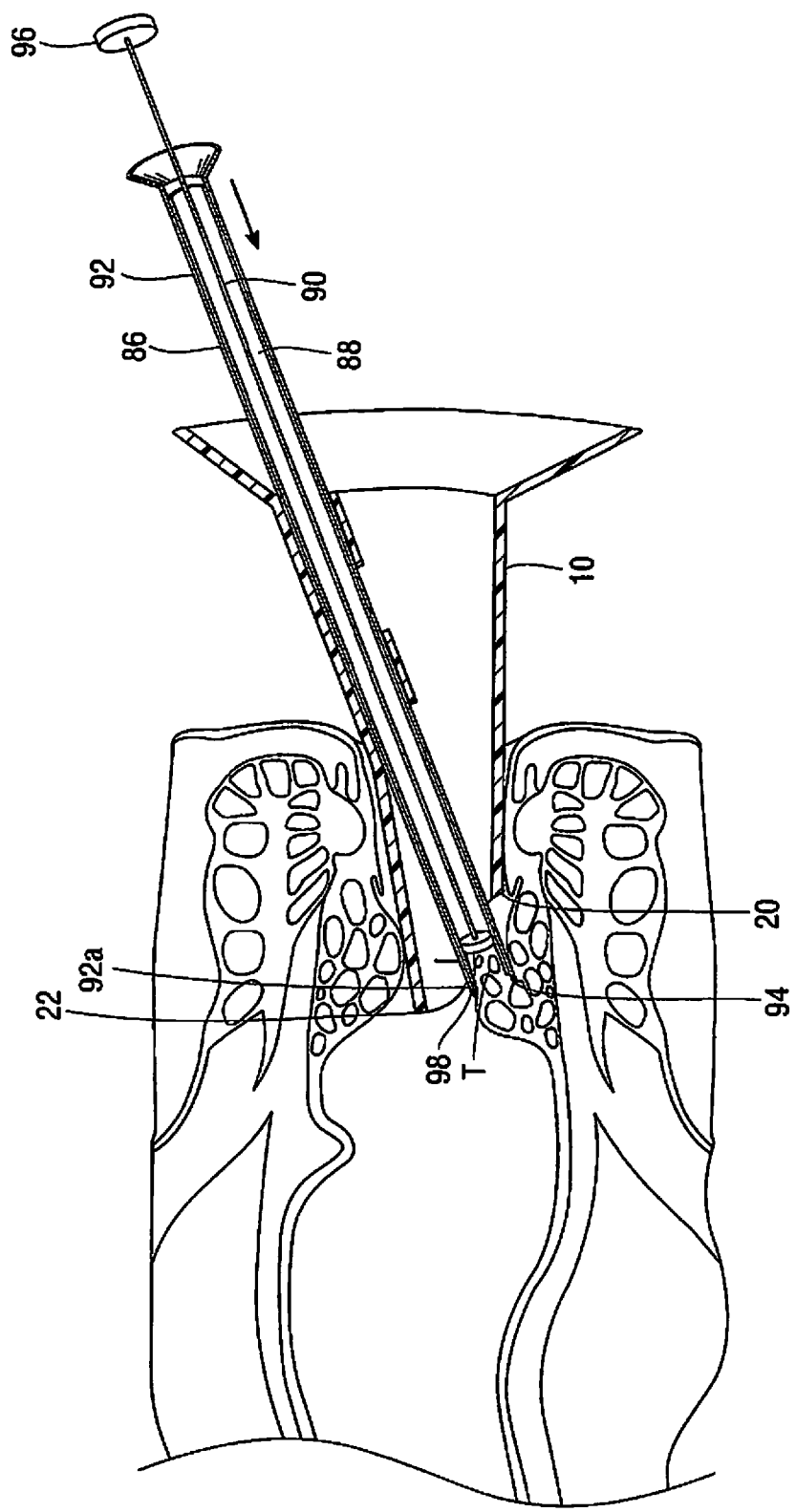
FIG. 12 is a view similar to FIG. 10 showing the outer tube advanced to advance the elastic band around the target tissue.
Figure 13:
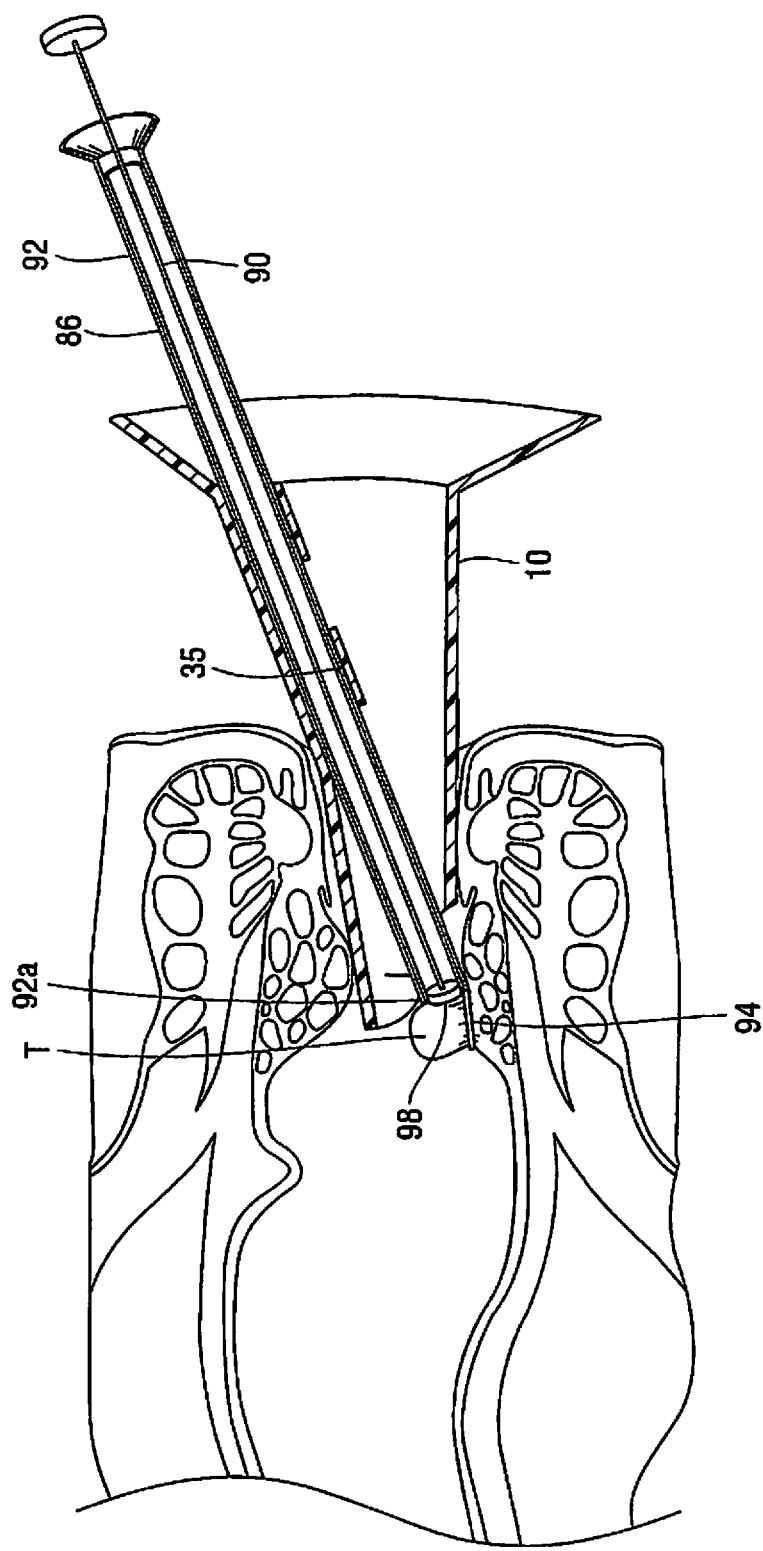
FIG. 13 is a view similar to FIG. 12 showing the plunger in the initial position and the elastic band placed around the target tissue.

Once the clinician is satisfied with the tissue suctioned within the inner tube 86, the outer tube (advancer) 92 is advanced distally in the direction of the arrow of FIG. 12 (as the inner tube 86 remains fixed) to push the elastic rubber band 94 as its distal end contacts (abuts) the elastic rubber band 94 supported on the exterior surface of the inner tube 86. The outer tube 92 is pushed forward until the elastic band 94 is pushed off (dislodged from) the inner tube 86. The elastic band 94 is thereby released onto the base of the suctioned tissue as shown in FIG. 13 to strangulate the target tissue.

Figure 14:
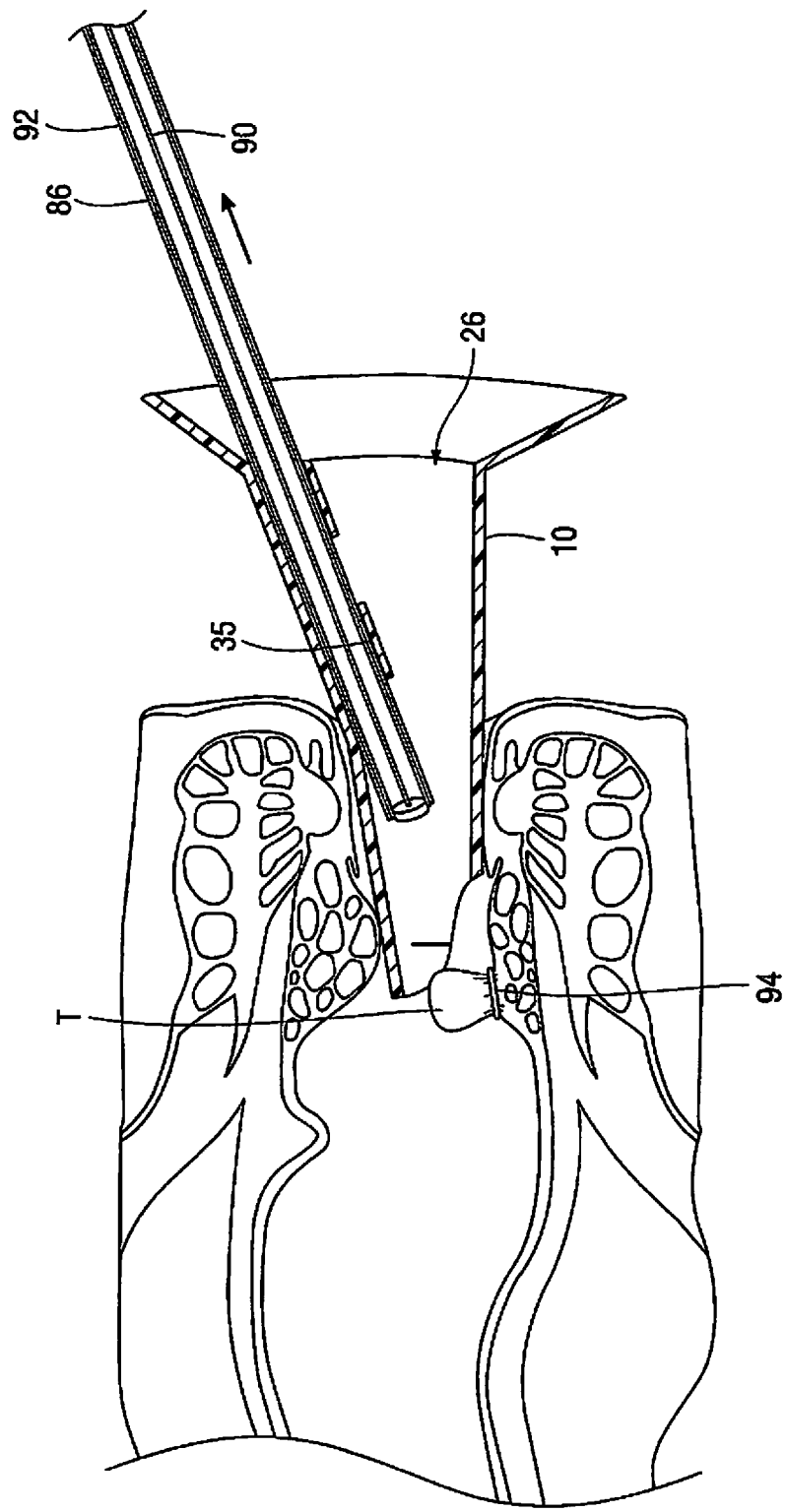
FIG. 14 is a view similar to FIG. 13 showing the ligation device being withdrawn from the anoscope.
Figure 15:
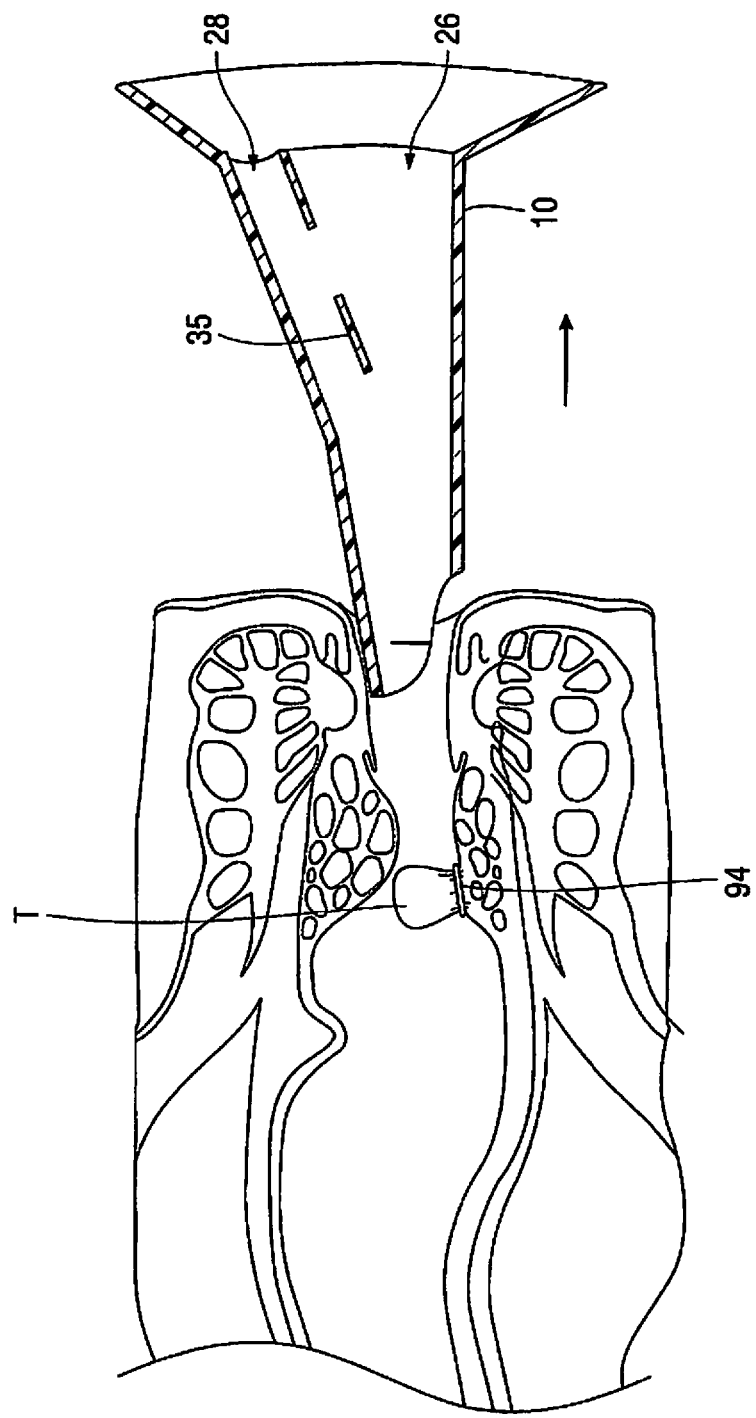
FIG. 15 is a view similar to FIG. 14 showing the anoscope being withdrawn from the rectum.

The ligating device 80 is then withdrawn proximally in the direction of the arrow of FIG. 14 for removal from the anoscope. After removal of the ligating device 80, the anoscope is then withdrawn proximally from the rectum in the direction of the arrow of FIG. 15.

If it is desired to treat another hemorrhoid, and the device 10 carries multiple elastic bands, the anoscope 10 and ligating device 80 are rotated to align the window of the anoscope with the target hemorrhoid tissue, the location of the anoscope 10 and ligating device 80 visualized with respect to the dentate line. Then the plunger 90 is retracted to suction the tissue into the lumen 88 of inner tube 86 followed by advancement of the outer tube 92 to release another elastic band 94 in accordance with the steps of the procedure illustrated in FIGS. 10-13 and depicted in the flow chart where if an additional hemorrhoid needs to be treated, it loops back to the procedure as shown. If it is desired to treat another hemorrhoid and the ligating device 10 carries only a single elastic band 94, the ligating device 80, with the anoscope 10 remaining in position, is withdrawn and another elastic band 94 is loaded onto the exterior surface of the inner tube 86 (The outer tube 92 can be retracted to leave a portion of the exterior surface exposed to provide room for mounting the elastic band 94). The ligating device 10 with the newly mounted elastic band 94 is then inserted thorough the anoscope 10, the tissue suctioned and the outer tube 92 advanced in the manner described above in conjunction with FIG. 9-13. The procedure can be repeated until all other internal hemorrhoids (typically a total of three) are treated.

Figure 21:
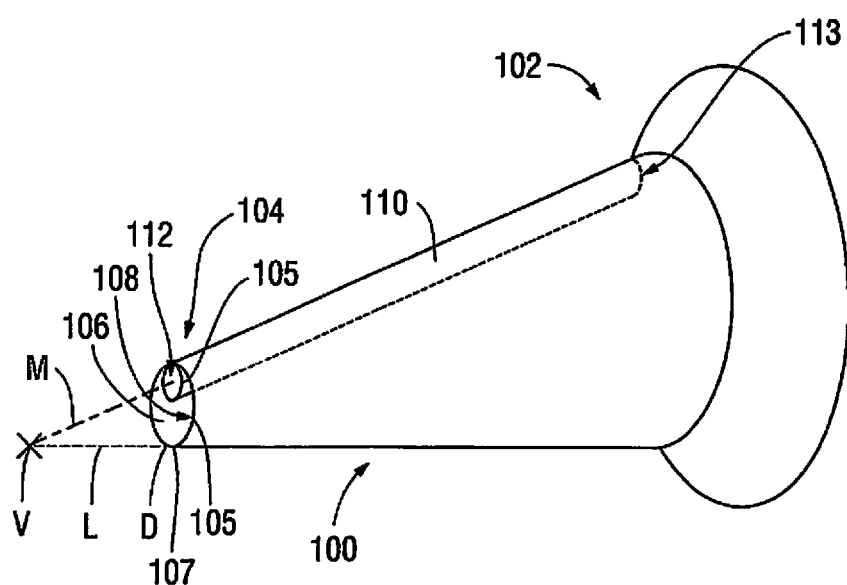
FIG. 21 is a side perspective view of an anoscope of another alternate embodiment of the present invention.
Figure 22A:
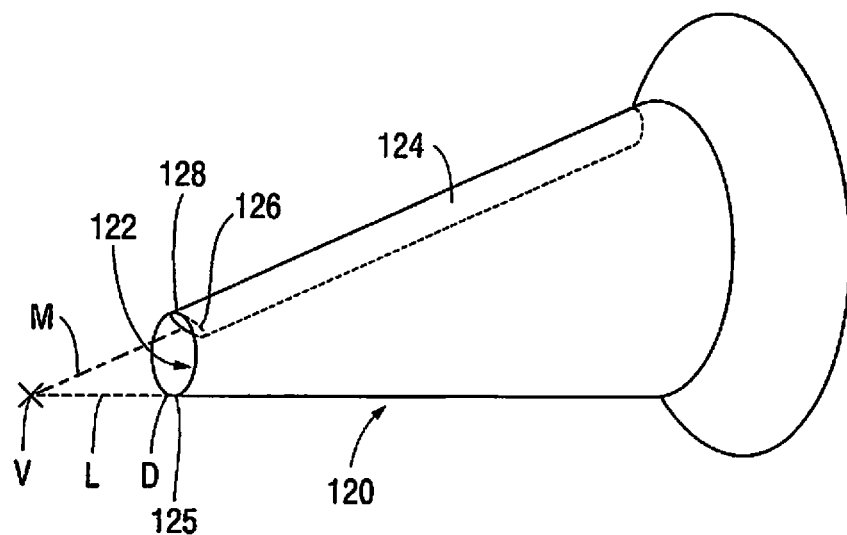
FIG. 22A is a side perspective view of an anoscope of another alternate embodiment of the present invention.
Figure 22B:
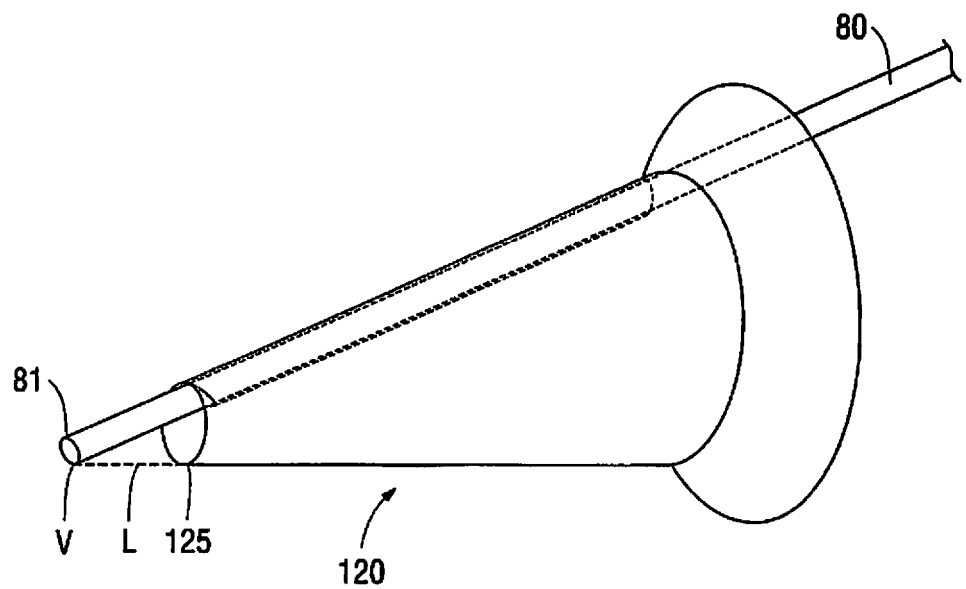
FIG. 22B is view similar to FIG. 22A showing a ligation device inserted through the channel with the tip a fixed distance proximal of the dentate line.

FIG. 21-22B illustrate alternate embodiments of the anoscope utilizing the angle of the second channel itself to ensure positioning of the ligating or other instrument anatomically proximal of the dentate line. More specifically, anoscope 100 of FIG. 21 has a proximal portion 102 and a distal portion 104, the wall of the anoscope tapering toward the distal portion 104. The anoscope 100 terminates at distal edge 105 and distal opening 106. The anoscope 100 has a channel (lumen) 108 dimensioned and configured to receive an obturator such as obturator 70 of FIG. 3A. The channel 108, like channel 26 of anoscope 10 discussed above, extends along a longitudinal axis of the anoscope 100. In the illustrated embodiment, the channel 108 has a transverse cross-section varying in diameter and shape along its length, however, different shaped channels and different shaped cross-sections, e.g., circular, oval, asymmetric, etc. are contemplated and can uniform or change (non-uniform) along the length.

Angled internal instrument channel (lumen) 110 forms a channel for receiving an instrument (device), e.g., the ligating device described herein. Channel 110 is cylindrical with a circular transverse cross-section, however, different shaped channels and different shaped cross-sections, e.g., oval, are also contemplated. Instrument channel 110 is preferably smaller in diameter than main channel 108. Channel 110 forms an acute angle with channel 108 and has a proximal opening 113 and a distal opening 112 terminating adjacent distal opening 106 of channel 108.

The walls of the anoscope 100 are configured and angled so that in use the target tissue (represented schematically by "X") is at a vertex of the triangle formed by the side of the anoscope. That is, the vertex V of the triangle is formed at the intersection of a) an imaginary line L extending (extrapolated) from the edge 107 (along the longitudinal axis of the edge) of anoscope 100 and b) the longitudinal axis of the angled channel 110 extended (extrapolated) distal of the distal edge 105 (imaginary line M). Thus, with the walls angled in such a way, the vertex V of the triangle where the target tissue is located is predictably located a fixed distance, e.g., about 2 cm to about 2.5 cm, proximal to the dentate line (represented by "D") of the patient which is positioned to be visible near the edge 105 of the anoscope 100. Therefore, a marker need not be utilized since in use, the clinician would insert the anoscope until the distal edge 105 is at the visualized dentate line (visualized with the naked eye as the clinician looks through channel 108). In this position, when an instrument is inserted through the angled (second) channel 110, the tip of the instrument when contacting the target tissue would be about 2 cm to about 2.5 cm anatomically proximal from the dentate line (the distance from V to D). The instrument could be locked to the anoscope in this position utilizing the interlocking structure discussed above.

The anoscope 120 of FIG. 22A is identical to the anoscope 100 of FIG. 21 except that angled instrument channel 124 has a slanted or angled distal tip 126 at edge 128. That is, edge 128 angles proximally to increase visibility by limiting the blocking of the view through the main channel (lumen) 122. In all other respects, anoscope 120 is identical to anoscope 100 so further discussion is not warranted as the features and use of anoscope 100 described herein are fully applicable to anoscope 120. The line L (extrapolated from edge 125) and vertex V are also shown in FIG. 22A to illustrate the predictable positioning of the instrumentation anatomically proximal of the dentate line (the distance from dentate line D to vertex V formed at the intersection of imaginary extrapolated lines L and M which in preferred embodiments is between about 2 cm to about 2.5 cm). FIG. 22B shows a ligating instrument, e.g., ligating instrument 80, inserted through the anoscope 120 to illustrate the distal tip 81 of instrument 80 at the vertex V of the imaginary triangle. Both anoscopes 100 and 120 can include a flange as illustrated as in the other embodiments described herein.

Note the channels 110 and 124 can open partially or fully outside/distal to the anoscope 100. Also, as an alternative to the continuous channel shown, channel 110 or 124 can be non-continuous, have an elongated slot so it is U or C-shaped, etc. as in the various embodiments of the channels discussed above and illustrated in the drawings. Thus, these variations of the angled instrument channel discussed above are applicable to channels 110 and 124 of the anoscope 100 and 120, respectively.

While the above description contains many specifics, those specifics should not be construed as limitations on the scope of the disclosure, but merely as exemplifications of preferred embodiments thereof. For example, those skilled in the art will envision many other possible variations that are within the scope and spirit of the disclosure as defined by the claims appended hereto.

What is claimed is:

1. An anoscope comprising: an outer wall dimensioned and configured for insertion into the anal canal, a lumen within the outer wall, a proximal end, a distal end, a first channel and a second channel, the first channel extending longitudinally through the anoscope, the first channel having a proximal opening and a distal opening, the second channel positioned within the lumen of the outer wall of the anoscope and at an angle to a longitudinal axis of the first channel, the second channel having a proximal opening and a distal opening, the distal opening of the second channel communicating with the first channel, wherein the second channel is on a first side of the anoscope, and the distal end of the anoscope forms a window on a second side, the second channel dimensioned and configured to receive a treatment device for exit out the distal opening of the first channel, the angled second channel intersecting the first channel in a manner that the treatment device extends into the first channel to the window.

2. The anoscope of claim 1, wherein the proximal opening of the second channel is within the first channel.

3. The anoscope of claim 1, further comprising a stop to limit axial movement of the treatment device inserted through the second channel.

4. The anoscope of claim 1, further comprising a stop to limit rotational movement of the treatment device positioned in the second channel.

5. The anoscope of claim 4, wherein the stop limits axial movement of the treatment device.

6. The anoscope of claim 1, wherein a distal end of the first side is distal of an opposing end of the anoscope on the second side.

7. The anoscope of claim 1, wherein the second channel includes a wall having a plurality of fenestrations to provide spaced discrete longitudinally aligned channels.

8. The anoscope of claim 1, wherein the second channel includes a longitudinally extending slot to enable lateral insertion of the treatment device into the second channel.

9. The anoscope of claim 1, wherein the anoscope has a marker to indicate a distance from a dentate line of a patient.

10. The anoscope of claim 1, wherein the second channel has a longitudinally extending opening facing one of inferiorly or laterally with respect to the first channel.

11. The anoscope of claim 1, wherein the anoscope and the second channel are configured so that a tip of the device inserted through the second channel to a target tissue is positioned 2 cm to 2.5 cm from a distal edge of the anoscope positioned at a dentate line of a patient.

12. The anoscope of claim 1, wherein the second channel has a distal end terminating at a proximal portion of an angled wall of the anoscope.

13. The anoscope of claim 1, wherein the second channel terminates at a distal end of an angled wall of the anoscope.

14. A system for stabilizing an instrument during a hemorrhoid treatment procedure comprising: an anoscope having an outer wall, a first channel extending along a longitudinal axis of the anoscope to provide direct visualization to a clinician through a length of the first channel and a smaller diameter second channel positioned at an angle to the first channel and configured to direct the instrument inserted through the second channel at an angle to a longitudinal axis of the first channel to reduce obstruction of direct visualization through the first channel, wherein the second channel is on a first side of the anoscope, and a distal end of the anoscope forms a window on a second side, the angled second channel intersecting the first channel in a manner that the instrument extends into the first channel to the window, and an interlocking engagement structure configured to engage with the instrument inserted through the second channel to restrict axial movement of the instrument to thereby maintain an axial position of the instrument with respect to a dentate line of a patient and wherein the second channel includes structure to limit rotational movement of the instrument within the second channel.

15. The system of claim 14, wherein the second channel is non-continuous to provide openings for visualization of the instrument during insertion through the second channel.

16. The system of claim 14, wherein a distal end of the first side is distal of an opposing end of the anoscope on the second side.

17. The system of claim 14, wherein the second channel has a distal end terminating within the first channel.

18. The system of claim 14, wherein the second channel includes a longitudinally extending slot to enable lateral insertion of the instrument into the second channel.

19. The system of claim 14, wherein the second channel terminates adjacent a distal opening of the first channel.

* * * * *